United States Patent
Kitchen et al.

(10) Patent No.: US 9,951,118 B2
(45) Date of Patent: Apr. 24, 2018

(54) ENGINEERING ANTIVIRAL T CELL IMMUNITY THROUGH STEM CELLS AND CHIMERIC ANTIGEN RECEPTORS

(71) Applicant: The Regents of the University of California, Oakland, CA (US)

(72) Inventors: Scott G. Kitchen, Los Angeles, CA (US); Jerome A. Zack, Tarzana, CA (US); Otto O. Yang, Los Angeles, CA (US); Irvin Chen, Palos Verdes Estates, CA (US); Masakazu Kamata, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/908,476

(22) PCT Filed: Aug. 1, 2014

(86) PCT No.: PCT/US2014/049360
§ 371 (c)(1),
(2) Date: Jan. 28, 2016

(87) PCT Pub. No.: WO2015/017755
PCT Pub. Date: Feb. 5, 2015

(65) Prior Publication Data
US 2016/0194375 A1    Jul. 7, 2016

Related U.S. Application Data

(60) Provisional application No. 61/861,684, filed on Aug. 2, 2013.

(51) Int. Cl.
| | | |
|---|---|---|
| A01N 63/00 | (2006.01) |
| C07K 14/73 | (2006.01) |
| C07K 14/725 | (2006.01) |
| C12N 5/0783 | (2010.01) |
| A61K 35/17 | (2015.01) |
| A61K 35/28 | (2015.01) |
| C07K 16/10 | (2006.01) |
| C12N 5/0789 | (2010.01) |

(52) U.S. Cl.
CPC ........ *C07K 14/70514* (2013.01); *A61K 35/17* (2013.01); *A61K 35/28* (2013.01); *C07K 14/7051* (2013.01); *C07K 16/1045* (2013.01); *C12N 5/0636* (2013.01); *C12N 5/0647* (2013.01); *C07K 2317/622* (2013.01); *C07K 2317/76* (2013.01); *C07K 2319/03* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 8,637,024 B2* | 1/2014 | Ho | ................. | C07K 16/1063 |
| | | | | 424/136.1 |
| 9,464,131 B2* | 10/2016 | Chan-Hui | .......... | C07K 16/1045 |
| 9,475,862 B2* | 10/2016 | Connors | ........... | C07K 16/1063 |
| 2002/0111474 A1* | 8/2002 | Capon | ............... | C07K 14/7051 |
| | | | | 536/23.5 |
| 2003/0199093 A1 | 10/2003 | Finer et al. | | |
| 2003/0219463 A1 | 11/2003 | Falkenburg et al. | | |
| 2012/0201794 A1* | 8/2012 | Chen | ................ | A01K 67/0271 |
| | | | | 424/93.21 |

FOREIGN PATENT DOCUMENTS

| | | |
|---|---|---|
| AU | 200039393 | 10/2000 |
| WO | 2011038290 | 3/2011 |
| WO | 2012129514 A1 | 9/2012 |
| WO | 2013123061 A1 | 8/2013 |

OTHER PUBLICATIONS

Robert et al. Blood 1994;84:2878-89.*
Hudecek, et al,, "Adoptive T-cell therapy for B-cell malignancies", Oct. 1, 2009, pp. 517-532, vol. 2, No. 5, Publisher: Expert Rev Hematol.
International Search Report received in PCT/US2014/049360, dated Dec. 24, 2014.
Written Opinion received in PCT/US20141049360, dated Dec. 24, 2014.
Extended European Search Report received in EP14831222 dated Dec. 20, 2016.
Mitsuyasu, et al., "Prolonged survival and tissue trafficking following adoptive transfer of CD4zeta gene-modified autologous CD4+ and CD8+ T cells in human immunodef . . . ", Aug. 1, 2000, pp. 785-793, vol. 96, No. 3, Publisher: Blood.

* cited by examiner

*Primary Examiner* — Qian Janice Li
(74) *Attorney, Agent, or Firm* — Suzannah K. Sundby, Esq.; Canady + Lortz LLP

(57) ABSTRACT

The HIV-specific cytotoxic T lymphocyte (CTL) response is a critical component in controlling HIV replication and is an important part of the ultimate failure to eradicate the virus. Disclosed herein are methods for genetically enhancing the HIV-specific CTL response to allow long-term viral suppression or viral clearance. Human hematopoietic stem cells (HSCs) were genetically modified such that they differentiate into mature CTLs that will kill HIV infected cells. As disclosed herein, the functional effector cells are not human leukocyte antigen (HLA)-restricted. As disclosed herein, stem cells are transduced with non-HLA restricted chimeric antigen receptors (CARs) that allow the recognition of HIV or HIV-infected cells when expressed by a CTL. These CARs are hybrid molecules that contain an extracellular HIV recognition domain and an intracellular TCR-zeta signaling domain. The CTL response may be enhanced through the targeting of T cell inhibitory receptors. The methods and compositions disclosed herein may be used to engineer antiviral immunity and HIV-specific CTL responses in vivo. Also disclosed herein are methods and compositions for the treatment of chronic viral infections such as HIV.

26 Claims, 13 Drawing Sheets

A. Killing Susceptibility

B. Virus Suppression

─□─ Uninfected T1 + CD8-Control
─■─ Infected T1 + CD8-Control
─○─ Uninfected T1 + CD8-CAR
─●─ Infected T1 + CD8-CAR
─✕─ Infected T1 %p24+

─○─ Control
─△─ + Mismatched CTL
─□─ + Matched CTL
─●─ + CD8-Control
─▲─ + CD8-CAR

SEQUENCE LISTING

<160> NUMBER OF SEQ ID NOS: 16

<210> SEQ ID NO 1
<211> LENGTH: 12
<212> TYPE: DNA
<213> ORGANISM: Artificial Sequence
<220> FEATURE:
<223> OTHER INFORMATION: Based on human sequence

<400> SEQUENCE: 1
ggccctgggc cc                                                          12

<210> SEQ ID NO 2
<211> LENGTH: 104
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 3
<211> LENGTH: 143
<212> TYPE: PRT
<213> ORGANISM: Homo sapiens

<400> SEQUENCE: 3

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Gly Gln
            20                  25                  30

Met Lys Lys Pro Gly Glu Ser Met Arg Ile Ser Cys Arg Ala Ser Gly
        35                  40                  45

Tyr Glu Phe Ile Asp Cys Thr Leu Asn Trp Ile Arg Leu Ala Pro Gly
    50                  55                  60

Lys Arg Pro Glu Trp Met Gly Trp Leu Lys Pro Arg Gly Gly Ala Val
65                  70                  75                  80

Asn Tyr Ala Arg Pro Leu Gln Gly Arg Val Thr Met Thr Arg Asp Val
                85                  90                  95

Tyr Ser Asp Thr Ala Phe Leu Glu Leu Arg Ser Leu Thr Val Asp Asp
            100                 105                 110

Thr Ala Val Tyr Phe Cys Thr Arg Gly Lys Asn Cys Asp Tyr Asn Trp
        115                 120                 125

Asp Phe Glu His Trp Gly Arg Gly Thr Pro Val Ile Val Ser Ser
    130                 135                 140

```
<210> SEQ ID NO 4
<211> LENGTH: 107
<212> TYPE: PRT
<213> ORGANISM: Homo sapiens

<400> SEQUENCE: 4

Glu Leu Val Leu Thr Gln Ser Pro Gly Thr Leu Ser Leu Ser Ala Gly
1               5                   10                  15

Glu Arg Ala Thr Leu Ser Cys Arg Ala Ser Gln Ser Val Ser Ser Gly
            20                  25                  30

Ser Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
50                  55                  60

Gly Ser Gly Ser Gly Thr Asp Phe Thr Leu Thr Ile Gly Arg Leu Glu
65                  70                  75                  80

Pro Glu Asp Leu Ala Val Tyr Tyr Cys Gln Gln Tyr Gly Thr Ser Pro
                85                  90                  95

Tyr Thr Phe Gly Gln Gly Thr Lys Leu Glu Ile
            100                 105

<210> SEQ ID NO 5
<211> LENGTH: 150
<212> TYPE: PRT
<213> ORGANISM: Homo sapiens

<400> SEQUENCE: 5

Met Leu Leu Leu Val Thr Ser Leu Leu Leu Cys Glu Leu Pro His Pro
1               5                   10                  15

Ala Phe Leu Leu Ile Pro Leu Glu Gln Ser Gly Ala Glu Val Lys Lys
            20                  25                  30

Pro Gly Ser Ser Val Gln Val Ser Cys Lys Ala Ser Gly Gly Thr Phe
        35                  40                  45

Ser Met Tyr Gly Phe Asn Trp Val Arg Gln Ala Pro Gly His Gly Leu
50                  55                  60

Glu Trp Met Gly Gly Ile Ile Pro Ile Phe Gly Thr Ser Asn Tyr Ala
65                  70                  75                  80

Gln Lys Phe Arg Gly Arg Val Thr Phe Thr Ala Asp Gln Ala Thr Ser
                85                  90                  95

Thr Ala Tyr Met Glu Leu Thr Asn Leu Arg Ser Asp Asp Thr Ala Val
            100                 105                 110

Tyr Tyr Cys Ala Arg Asp Phe Gly Pro Asp Trp Glu Asp Gly Asp Ser
        115                 120                 125

Tyr Asp Gly Ser Gly Arg Gly Phe Phe Asp Phe Trp Gly Gln Gly Thr
    130                 135                 140

Leu Val Thr Val Ser Ser
145                 150

<210> SEQ ID NO 6
<211> LENGTH: 105
<212> TYPE: PRT
<213> ORGANISM: Homo sapiens

<400> SEQUENCE: 6

Gln Ser Ala Leu Thr Gln Pro Pro Ser Ala Ser Gly Ser Pro Gly Gln
1               5                   10                  15

Ser Ile Ser Ile Ser Cys Thr Gly Thr Ser Asn Arg Phe Val Ser Trp
            20                  25                  30
```

Tyr Gln Gln His Pro Gly Lys Ala Pro Lys Leu Val Ile Tyr Gly Val
            35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Ser Ser Leu Val Gly Asn Trp Asp Val Ile Phe
                85                  90                  95

Gly Gly Gly Thr Lys Leu Thr Val Leu
            100                 105

<210> SEQ ID NO 7
<211> LENGTH: 159
<212> TYPE: PRT
<213> ORGANISM: Homo sapiens

<400> SEQUENCE: 7

Met Leu Leu Leu Val Thr Ser Leu Leu Cys Glu Leu Pro His Pro
1               5                   10                  15

Ala Phe Leu Leu Ile Pro Gln Pro Gln Leu Gln Glu Ser Gly Pro Gly
                20                  25                  30

Leu Val Glu Ala Ser Glu Thr Leu Ser Leu Thr Cys Thr Val Ser Gly
            35                  40                  45

Asp Ser Thr Ala Ala Cys Asp Tyr Phe Trp Gly Trp Val Arg Gln Pro
    50                  55                  60

Pro Gly Lys Gly Leu Glu Trp Ile Gly Gly Leu Ser His Cys Ala Gly
65                  70                  75                  80

Tyr Tyr Asn Thr Gly Trp Thr Tyr His Asn Pro Ser Leu Lys Ser Arg
                85                  90                  95

Leu Thr Ile Ser Leu Asp Thr Pro Lys Asn Gln Val Phe Leu Lys Leu
            100                 105                 110

Asn Ser Val Thr Ala Ala Asp Thr Ala Ile Tyr Tyr Cys Ala Arg Phe
        115                 120                 125

Asp Gly Glu Val Leu Val Tyr His Asp Trp Pro Lys Pro Ala Trp Val
    130                 135                 140

Asp Leu Trp Gly Arg Gly Thr Leu Val Thr Val Ser Ser
145                 150                 155

<210> SEQ ID NO 8
<211> LENGTH: 105
<212> TYPE: PRT
<213> ORGANISM: Homo sapiens

<400> SEQUENCE: 8

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
                20                  25                  30

Tyr Gln Gln His Ala Gly Lys Ala Pro Lys Leu Val Ile Tyr Asp Val
            35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

```
Ala Val Tyr Tyr Cys Gly Ser Leu Val Gly Asn Trp Asp Val Ile Phe
                85                  90                  95
Gly Gly Gly Thr Lys Leu Thr Val Leu
            100                 105

<210> SEQ ID NO 9
<211> LENGTH: 157
<212> TYPE: PRT
<213> ORGANISM: Homo sapiens

<400> SEQUENCE: 9

Met Leu Leu Leu Val Thr Ser Leu Leu Cys Glu Leu Pro His Pro
1               5                   10                  15

Ala Phe Leu Leu Ile Pro Gln Pro Gln Leu Gln Glu Ser Gly Pro Thr
                20                  25                  30

Leu Val Glu Ala Ser Glu Thr Leu Ser Leu Thr Cys Ala Val Ser Gly
            35                  40                  45

Asp Ser Thr Ala Ala Cys Asn Ser Phe Trp Gly Trp Val Arg Gln Pro
50                  55                  60

Pro Gly Lys Gly Leu Glu Trp Val Gly Ser Leu Ser His Cys Ala Ser
65                  70                  75                  80

Tyr Trp Asn Arg Gly Trp Thr Tyr His Asn Pro Ser Leu Lys Ser Arg
                85                  90                  95

Leu Thr Leu Ala Leu Asp Thr Pro Lys Asn Leu Val Phe Leu Lys Leu
            100                 105                 110

Asn Ser Val Thr Ala Ala Asp Thr Ala Thr Tyr Tyr Cys Ala Arg Phe
            115                 120                 125

Gly Gly Glu Val Leu Arg Tyr Thr Asp Trp Pro Lys Pro Ala Trp Val
            130                 135                 140

Asp Leu Trp Gly Arg Gly Thr Leu Val Thr Val Ser Ser
145                 150                 155

<210> SEQ ID NO 10
<211> LENGTH: 110
<212> TYPE: PRT
<213> ORGANISM: Homo sapiens

<400> SEQUENCE: 10

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
                20                  25                  30

Glu Ser Val Ser Trp Tyr Gln Gln His Pro Gly Lys Ala Pro Lys Val
            35                  40                  45

Val Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
            100                 105                 110

<210> SEQ ID NO 11
<211> LENGTH: 158
<212> TYPE: PRT
<213> ORGANISM: Homo sapiens
```

<400> SEQUENCE: 11

Met Leu Leu Leu Val Thr Ser Leu Leu Leu Cys Glu Leu Pro His Pro
1               5                   10                  15

Ala Phe Leu Leu Ile Pro Gln Arg Leu Val Glu Ser Gly Gly Gly Val
            20                  25                  30

Val Gln Pro Gly Ser Ser Leu Arg Leu Ser Cys Ala Ala Ser Gly Phe
        35                  40                  45

Asp Phe Ser Arg Gln Gly Met His Trp Val Arg Gln Ala Pro Gly Gln
    50                  55                  60

Gly Leu Glu Trp Val Ala Phe Ile Lys Tyr Asp Gly Ser Glu Lys Tyr
65                  70                  75                  80

His Ala Asp Ser Val Trp Gly Arg Leu Ser Ile Ser Arg Asp Asn Ser
                85                  90                  95

Lys Asp Thr Leu Tyr Leu Gln Met Asn Ser Leu Arg Val Glu Asp Thr
            100                 105                 110

Ala Thr Tyr Phe Cys Val Arg Glu Ala Gly Gly Pro Asp Tyr Arg Asn
        115                 120                 125

Gly Tyr Asn Tyr Tyr Asp Phe Tyr Asp Gly Tyr Tyr Asn Tyr His Tyr
    130                 135                 140

Met Asp Val Trp Gly Lys Gly Thr Thr Val Thr Val Ser Ser
145                 150                 155

<210> SEQ ID NO 12
<211> LENGTH: 109
<212> TYPE: PRT
<213> ORGANISM: Homo sapiens

<400> SEQUENCE: 12

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 13
<211> LENGTH: 153
<212> TYPE: PRT
<213> ORGANISM: Homo sapiens

<400> SEQUENCE: 13

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Lys Pro Gly Gly Ser Leu Arg Leu Ser Cys Ser Ala Ser Gly
        35                  40                  45

```
Phe Asp Phe Asp Asn Ala Trp Met Thr Trp Val Arg Gln Pro Pro Gly
        50                  55                  60

Lys Gly Leu Glu Trp Val Gly Arg Ile Thr Gly Pro Gly Glu Gly Trp
 65                  70                  75                  80

Ser Val Asp Tyr Ala Ala Pro Val Glu Gly Arg Phe Thr Ile Ser Arg
                85                  90                  95

Leu Asn Ser Ile Asn Phe Leu Tyr Leu Glu Met Asn Asn Leu Arg Met
                100                 105                 110

Glu Asp Ser Gly Leu Tyr Phe Cys Ala Arg Thr Gly Lys Tyr Tyr Asp
            115                 120                 125

Phe Trp Ser Gly Tyr Pro Pro Gly Glu Glu Tyr Phe Gln Asp Trp Gly
        130                 135                 140

Arg Gly Thr Leu Val Thr Val Ser Ser
145                 150

<210> SEQ ID NO 14
<211> LENGTH: 105
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
  1               5                  10                  15

Asp Thr Val Thr Ile Thr Cys Gln Ala Asn Gly Tyr Leu Asn Trp Tyr
                20                  25                  30

Gln Gln Arg Arg Gly Lys Ala Pro Lys Leu Leu Ile Tyr Asp Gly Ser
            35                  40                  45

Lys Leu Glu Arg Gly Val Pro Ser Arg Phe Ser Gly Arg Arg Trp Gly
 50                  55                  60

Gln Glu Tyr Asn Leu Thr Ile Asn Asn Leu Gln Pro Glu Asp Ile Ala
 65                  70                  75                  80

Thr Tyr Phe Cys Gln Val Tyr Glu Phe Val Val Pro Gly Thr Arg Leu
                85                  90                  95

Asp Leu Lys Arg Thr Val Ala Ala Pro
                100                 105

<210> SEQ ID NO 15
<211> LENGTH: 151
<212> TYPE: PRT
<213> ORGANISM: Homo sapiens

<400> SEQUENCE: 15

Met Leu Leu Leu Val Thr Ser Leu Leu Leu Cys Glu Leu Pro His Pro
  1               5                  10                  15

Ala Phe Leu Leu Ile Pro Gln Val Gln Leu Gln Ser Gly Ala Ala
                20                  25                  30

Val Thr Lys Pro Gly Ala Ser Val Arg Val Ser Cys Glu Ala Ser Gly
            35                  40                  45

Tyr Asn Ile Arg Asp Tyr Phe Ile His Trp Trp Arg Gln Ala Pro Gly
 50                  55                  60

Gln Gly Leu Gln Trp Val Gly Trp Ile Asn Pro Lys Thr Gly Gln Pro
 65                  70                  75                  80

Asn Asn Pro Arg Gln Phe Gln Gly Arg Val Ser Leu Thr Arg His Ala
                85                  90                  95

Ser Trp Asp Phe Asp Thr Phe Ser Phe Tyr Met Asp Leu Lys Ala Leu
                100                 105                 110
```

```
Arg Ser Asp Asp Thr Ala Val Tyr Phe Cys Ala Arg Gln Arg Ser Asp
            115                 120                 125

Tyr Trp Asp Phe Asp Val Trp Gly Ser Gly Thr Gln Val Thr Val Ser
    130                 135                 140

Ser Ala Ser Thr Lys Gly Pro
145                 150

<210> SEQ ID NO 16
<211> LENGTH: 15
<212> TYPE: DNA
<213> ORGANISM: Artificial Sequence
<220> FEATURE:
<223> OTHER INFORMATION: Primer based on human sequence

<400> SEQUENCE: 16
ggggsggggs ggggs                                               15
```

ENGINEERING ANTIVIRAL T CELL IMMUNITY THROUGH STEM CELLS AND CHIMERIC ANTIGEN RECEPTORS

CROSS-REFERENCE TO RELATED APPLICATIONS

This application claims the benefit of U.S. Application No. 61/861,684, filed 2 Aug. 2013, which is herein incorporated by reference in its entirety.

ACKNOWLEDGEMENT OF GOVERNMENT SUPPORT

This invention was made with Government support under AI028697, AI070010, and AI078806, awarded by the National Institutes of Health. The Government has certain rights in the invention.

REFERENCE TO A SEQUENCE LISTING SUBMITTED VIA EFS-WEB

The content of the ASCII text file of the sequence listing named "20140731_034044_128WO1_seq_ST25" which is 16.7 KB in size was created on 31 Jul. 2014 and electronically submitted via EFS-Web herewith the application is incorporated herein by reference in its entirety.

BACKGROUND OF THE INVENTION

1. Field of the Invention

The present invention generally relates to recombinant human progenitor cells, and engineered functional effector cells including engineered human thymocytes, and engineered human T cells, and methods of treating subjects therewith.

2. Description of the Related Art

CD8+ cytotoxic T-lymphocytes (CTLs) partially control human immunodeficiency virus (HIV) in almost all infected persons, but eventually fail due to viral mutation, down-regulation of Human Leukocyte Antigen (HLA), lack of CD4+ T-cell help, and CTL clonal exhaustion. While HIV infections can be controlled in many individuals with anti-retroviral drugs, these are expensive and associated with significant toxicities. Due to viral reservoirs, if therapy is terminated, virus replication and disease progression resume, requiring patients to remain on these medications permanently. To date there has only been a single reported case of cured chronic HIV infection in an adult, via bone marrow transplant from a donor lacking the normal gene for C-C chemokine receptor type 5 (CCR5), which is a cell receptor required for most strains of HIV to infect cells. However, the mortality rate of this procedure is about 40%, and matched bone marrow with this genetic profile is almost nonexistent for most ethnic groups, rendering this approach impractical for broader clinical applicability. Several recent studies have attempted to remove CCR5 from hematopoietic stem cells and/or deliver anti-HIV genes to protect cells from HIV infection in humans, but these studies face limitations due to unknowns regarding levels of transduced cell engraftment required to generate an HIV-resistant immune system.

SUMMARY OF THE INVENTION

In some embodiments, the present invention is directed to a recombinant progenitor cell which comprises a stem cell transduced with a vector containing a nucleic acid molecule which encodes a chimeric antigen receptor (CAR) specific for a virus or an epitope thereof, wherein the recombinant progenitor cell is capable of differentiating into a functional effector cell. In some embodiments, the nucleic acid molecule is contained within a CAR construct according to the present invention. In some embodiments, the stem cell is a hematopoietic stem cell or a hematopoietic progenitor cell. In some embodiments, the stem cell is a memory T stem cell (such as central memory T cell, an effector memory T cell, or a stem cell memory T cell). In some embodiments, the vector is a lentiviral vector. In some embodiments, the chimeric antigen receptor comprises, consists essentially of, or consists of CD4 extracellular and transmembrane domains and a CD3 zeta signaling domain (CD4ζ). In some embodiments, the CD4 extracellular domain binds gp120 expressed on the surface of cells infected with HIV. In some embodiments, the virus is an immunodeficiency virus such as HIV or SIV. In some embodiments, the virus is a lentivirus. In some embodiments, the lentivirus is a human immunodeficiency virus. In some embodiments, the functional effector cell is a T-cell. In some embodiments, the T-cell expresses CD4ζ CAR on its cell surface. In some embodiments, the vector further comprises one or more genetic sequences which protect the recombinant progenitor cell from infection by the virus and/or inhibit infection by the virus. In some embodiments, the genetic sequences are selected from the group consisting of: sh1005, sh516, and a nucleic acid molecule encoding C46.

In some embodiments, the present invention is directed to a method of producing a functional effector cell which comprises differentiating or developing the recombinant progenitor cell of the present invention and then maturing it into the functional effector cell. In some embodiments, the nucleic acid molecule is contained within a CAR construct according to the present invention. In some embodiments, the recombinant progenitor comprises a stem cell transduced with a vector containing a nucleic acid molecule which encodes a chimeric antigen receptor (CAR) specific for a virus or an epitope thereof. In some embodiments, the stem cell is a hematopoietic stem cell or a hematopoietic progenitor cell. In some embodiments, the stem cell is a memory T stem cell (such as central memory T cell, an effector memory T cell, or a stem cell memory T cell). In some embodiments, the vector is a lentiviral vector. In some embodiments, the chimeric antigen receptor comprises, consists essentially of, or consists of CD4 extracellular and transmembrane domains and a CD3 zeta signaling domain (CD4ζ). In some embodiments, the CD4 extracellular domain binds gp120 expressed on the surface of cells infected with HIV. In some embodiments, the virus is an immunodeficiency virus such as HIV or SIV. In some embodiments, the virus is a lentivirus. In some embodiments, the lentivirus is a human immunodeficiency virus. In some embodiments, the functional effector cell is a T-cell. In some embodiments, the T-cell expresses CD4ζ CAR on its cell surface. In some embodiments, the vector further comprises one or more genetic sequences which protect the recombinant progenitor cell from infection by the virus and/or inhibit infection by the virus. In some embodiments, the genetic sequences are selected from the group consisting of: sh1005, sh516, and a nucleic acid molecule encoding C46. In some embodiments, the recombinant progenitor cell is administered to or engrafted in a subject. In some embodiments, the subject is mammalian. In some embodiments, the subject is a model animal such as a mouse or a non-human primate. In some embodiments, the subject is a human subject. In some embodiments, the recombinant progenitor cell is subjected to the thymus tissue of the subject. In some embodiments, the present invention is directed to an engineered functional effector cell made by the method according to the present invention. In some embodiments, the engineered functional effector cell expresses CD4ζ CAR on its cell surface.

In some embodiments, the present invention is directed to a method of inhibiting, reducing, or treating a viral infection in a subject which comprises administering the recombinant progenitor cell according to the present invention and/or the engineered functional effector cell according to the present invention to the subject. In some embodiments, the subject is mammalian. In some embodiments, the subject is a model animal such as a mouse or a non-human primate. In some embodiments, the subject is a human subject.

In some embodiments, the recombinant progenitor cells and engineered functional effector cells according to the present invention lack HLA-restricted T cell receptors.

In some embodiments, the present invention is directed to a CAR construct, i.e., a nucleic acid molecule which comprises a sequence encoding CD4, preferably human CD4, fused to the signaling domain of the CD3 complex ζ-chain. In some embodiments, the nucleic acid molecule is selected from the group consisting of CAR constructs, Double CAR constructs, Triple CAR constructs, truncated CAR constructs, truncated Double CAR constructs, truncated Triple CAR constructs, and second generation CAR constructs. In some embodiments, the nucleic acid molecule is CD4ζ CAR, Double CAR C46, Triple CD4ζ CAR, CD4D1D2D3CAR, CD4D1D2CAR, or CD4D1CAR. In some embodiments, the nucleic acid molecule contains a nucleotide sequence encoding a single chain antibody having an amino acid sequence selected from the group consisting of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; and SEQ ID NO:15.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

DETAILED DESCRIPTION OF THE INVENTION

The present invention provides a method for programming stem cells to provide a self-renewing population of both CD8+ and CD4+ HIV-targeted T-cells that are resistant to direct HIV infection, and which bypass the mechanisms by which HIV usually evades the immune response. The present invention involves the genetic modification of hematopoietic stem cells (HSCs), hematopoietic progenitor cells (HPCs), or hematopoietic stem and progenitor cells (HSPCs) using chimeric antigen receptors (CARs) to form antigen-specific T cells against HIV.

Modification of human HSCs with a T-cell receptor (TCR) comprising an alpha and beta chain (which bind HIV peptide in the context of an HLA molecule) allows the differentiation of HIV-specific T cells in vivo in humanized mice. See Kitchen et al. (2012) PLoS Pathog. 8(4): e1002649; see also U.S. Ser. No. 13/045,073, filed 10 Mar. 2011, both of which are herein incorporated by reference in their entirety. The engineered T cells, however, are human leukocyte antigen (HLA) restricted.

The present invention utilizes CARs specific for HIV in place of T cell receptors (TCRs). CARs have an antigen binding domain specific for HIV and an internal TCR signaling domain. When they bind the target antigen, which occurs directly without HLA, they trigger the cell like a TCR. Unlike natural T cell receptors, CARs do not need to recognize HLA molecules to detect antigen. Thus, the engineered T cells according to the present invention are not HLA restricted. Consequently, the CAR constructs and engineered cells according to the present invention need not be matched to a subject's genetic HLA profile for effectively treating the subject. Thus, treatments according to the present invention may be used in HIV infected persons of any HLA types.

Figure 1:
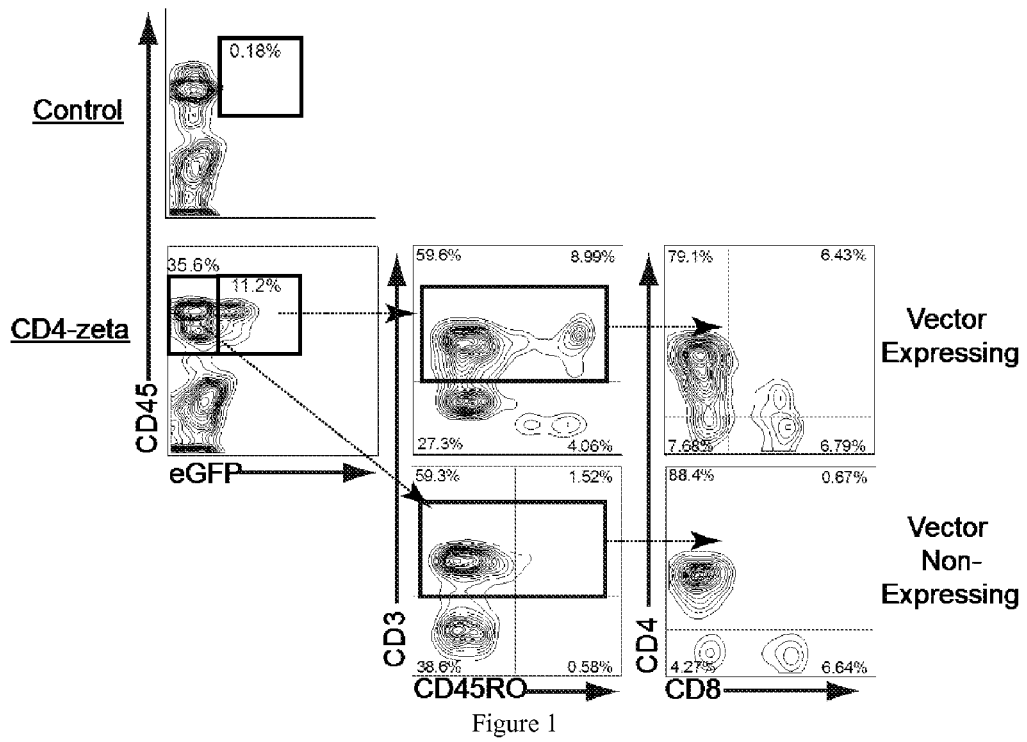
FIG. 1 are graphs showing that CD4ζ CAR allows differentiation of T cells from stem cells.

The CAR used as an example herein comprises human CD4 external domain fused to the CD3-zeta signaling region on the T-cell receptor (which mediates T cell activation). Prior to the present invention, it was thought that artificially having the CD4-zeta expressed on the surface of a developing T cell would cause aberrant signaling which would cause the cell to fail the development process because CD4 and the zeta chain component are involved in the proper development of T cells from stem cells. As shown in FIG. 1, HSPCs transduced with a CAR construct comprising human CD4 fused to the CD3 zeta-signaling region on the T-cell receptor allows the differentiation of HIV-specific T cells in vivo and exhibit normal function in humanized mice. Specifically, human CD34+ HSCs were transduced with a lentiviral vector containing the CD4ζ CAR and eGFP reporter and these cells were implanted into humanized mice (NSG strain). Twelve weeks following implantation, peripheral blood was analyzed for expression of human CD45 and the eGFP reporter gene (left column) in mice that either received no vector (control) (top panel) and mice that received cells that were transduced (middle and bottom panels). In mice receiving vector transduced cells, vector expressing cells (middle panels) and cells not expressing vector (bottom panels) were analyzed for the human T cell marker CD3, human differentiation marker CD45 RO (middle column). Human T cells expressing CD3 were further analyzed for expression of CD4 and CD8 (right column). These results indicate that cells expressing the CD4ζ CAR are capable of undergoing differentiation from stem cells into mature T cells. Surprisingly, CAR expression did not substantially alter the differentiation or lineage commitment of developing T-cells.

Thus, in some embodiments, the present invention is directed to methods of genetically engineering and enhancing the human cellular immune response against HIV, preferably Human Immunodeficiency Virus Type 1 (HIV-1), using CARs specific to HIV. These CARs are engineered T-cell receptors (TCRs) which comprise or consist of an HIV, preferably an HIV-1, envelope recognition domain, a transmembrane domain, and an intracellular signaling domain that direct T-cells to kill HIV-infected cells. As such, the CARs according to the present invention are freed from a drawback of natural TCRs for gene therapy—HLA restriction.

Treatments according to the present invention include one-time dosing, or an infrequent procedure involving stem cell mobilization, purification, culture, lentiviral transduction, and infusion. Treatments may be by administration of a gene delivery vector, e.g., lentivirus, containing a gene encoding a CAR according to the present invention and/or administration of stem cells genetically modified to express one or more CARs according to the present invention. In some embodiments, the gene delivery vector is designed to deliver the gene into stem cells. In some embodiments, the stem cells are HSCs, HPCs, or both. In some embodiments, treatments according to the present invention do not suffer from low-levels of transduced cell engraftment that limits other stem cell therapeutic approaches due to the fact that, even at low stem cell engraftment frequencies, CAR-containing T-cells are expected to proliferate in the periphery in response to HIV, preferably HIV-1, antigens. This harnesses the natural proliferative capacity of stem cells and mature T cell progeny to generate key antiviral effector cells.

The methods of the present invention may be used to treat any infected subject, preferably mammalian subjects, more preferably human subjects, including those with HIV stably suppressed by highly active antiretroviral therapy (HAART), and/or clear latent viral reservoirs. In some embodiments, the subjects to be treated are those who are failing standard antiretroviral therapy due to drug resistance, unable to tolerate the complications or side effects of antiretroviral drugs, and/or unwilling or unable logistically to take life-long antiretroviral therapy.

According to the present invention, delivery of CARs to stem cells will provide a non-exhaustible source of CD4+ and CD8+ T and NK cells specific for HIV, preferably HIV-1, to recognize and kill cells infected with HIV in vivo, as opposed to natural cellular immunity that faces clonal exhaustion. Furthermore, T-cells made by the method of the present invention are superior to T-cells obtained using other methods in the art, because the CARs are HLA-independent, and are therefore broadly applicable to any person, and not subject to a key immune evasion strategy of HLA down-regulation by HIV infected cells.

The genetic modification of HSCs with a CAR in subjects will result in the production of mature effector cells that can lower viral loads in the infected subjects and promote the eradication of the virus. Although there are a variety of models known in the art that can be employed to test and screen various embodiments of the present invention, the non-human primate model (NHP) of simian immunodeficiency virus (SIV) and chimeric simian-human immunodeficiency virus (SHIV) infection, which has been an important surrogate system in the understanding of HIV pathogenesis, disease progression, and in the development of antiretroviral therapeutic and vaccine strategies, may be employed as described herein.

SHIV chimeras are created by inserting HIV-1 genes, for instance env, rev, tat, and vpu, into a background of SIVmac. Such "env-SHIVs" readily infect macaques, and offer all the advantages of the SIVmac/macaque model. An example of a SHIV chimera is the CCR5-tropic subtype C SHIV-1157ipd3N4 (referred to as SHIV-C). Infected macaques develop CD4+ T-cell loss usually in a few weeks and develop AIDS at intervals ranging from a few weeks to two years. Histological changes in lymphoid and other tissues closely resemble those seen in human AIDS. Thus, the SHIV/macaque model is a superb model to study novel HIV/AIDS treatment strategies.

The present invention offers several advantages over current therapeutic modalities. First, as it involves long-lived stem cells, treatments should require only a single administration. The risk of undesirable T-cell reactivity would be minimized, as stem cell-derived T-cells will pass through thymic selection. As both CD4 and CD8 cells arise from CAR-transduced stem cells, there will be both anti-HIV CD4− (helper) and CD8− (CTL) T-cell function. Finally, as new HIV/SHIV-specific cells are constantly renewed from stem cells, HIV production from activation of HIV/SHIV reservoir cells can be contained and prevented from systemic spread.

Preliminary Studies

Figure 2:
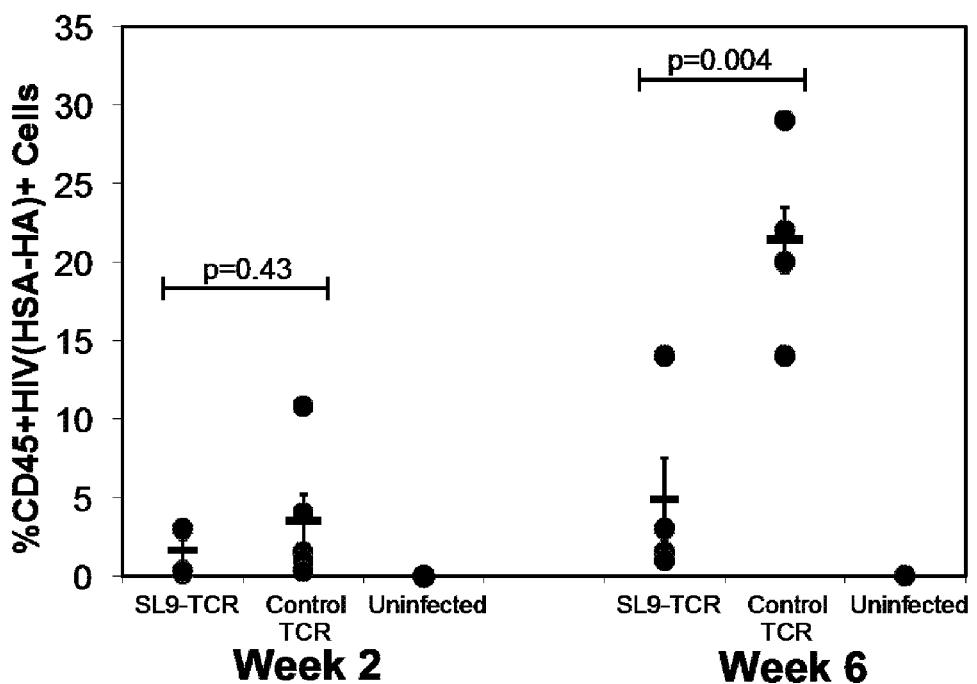
FIG. 2 is a graph showing suppression of HIV replication by HIV-TCR containing T cells.

A surrogate humanized bone marrow, fetal liver and thymus (BLT) mouse model was used to demonstrate that human CD34+ HSCs can be genetically modified with a lentiviral vector containing a molecularly cloned TCR specific to HIV (HIV-TCR construct), and subsequently develop into mature, fully functional CTL using methods known in the art. Humanized mice containing the HIV-TCR construct (SL-9) or control TCR were infected with the HIV reporter virus and were assessed for human CD45+ cells expressing HIV by flow cytometry for the HSA-HA marker gene encoded by the virus genome. As shown in FIG. 2, The HIV-TCR construct significantly suppresses HIV expressing cells in vivo.

Figure 3:
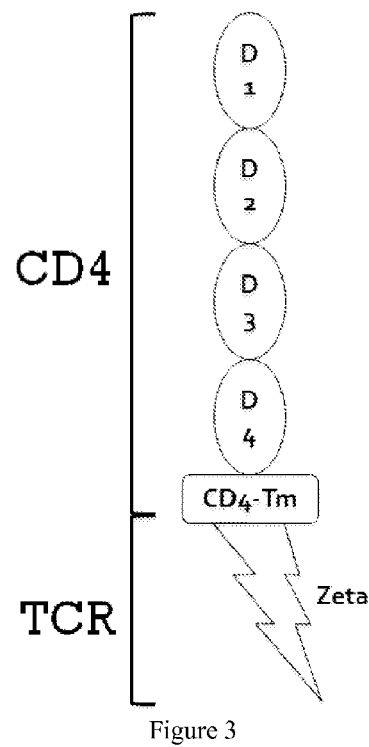
FIG. 3 is a schematic representation of the CD4ζ chimeric antigen receptor.

To determine whether stem cells transduced with a vector containing a CAR specific to HIV (CAR construct), can develop into functional effector cells, CD4ζ CAR was used. FIG. 3 schematically shows CD4ζ CAR, which is a fusion molecule of human CD4 with the signaling domain of the CD3 complex ζ-chain. This harnesses CD4 as a recognition receptor for HIV gp120 envelope on the surface of infected cells; engagement of CD4 triggers T-cell recognition of infected cells through ζ-chain signaling.

Figure 4A:
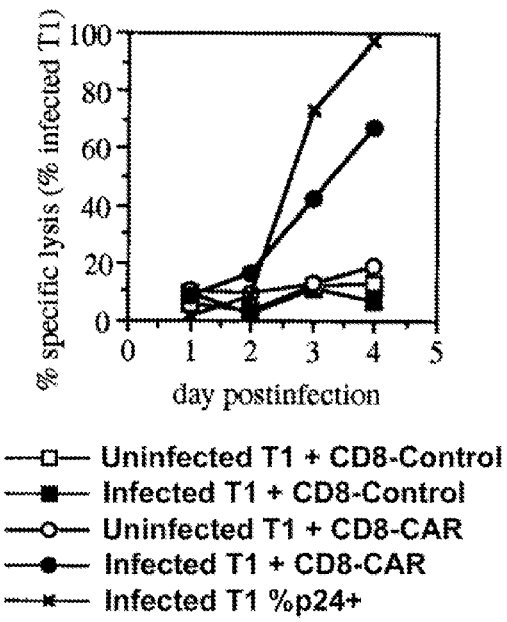
FIG. 4A is a graph showing the ability of CD4ζ CAR transduced T cells to kill HIV infected T1 cells.
Figure 4B:
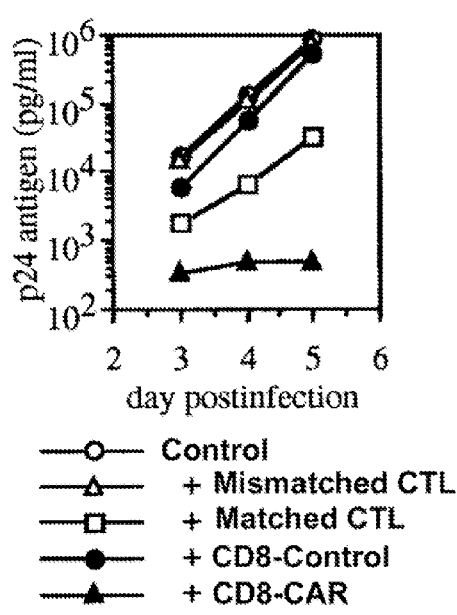
FIG. 4B is a graph showing the ability of by HLA-I matched or mismatched CTL clones, and CD4ζ CAR transduced CD8+ T cells to suppress viral replication.

HIV infected T1 cells were tested for susceptibility to killing by T cells transduced with the CD4ζ CAR construct. HIV-infected T1 cells were tested for killing by HLA-I matched or mismatched CTL clones (i.e., having the HIV-TCR construct) or CD4ζ transduced CD8+ T cells (i.e., having the CAR construct). As shown in FIG. 4A and FIG. 4B, CD8+ T-cells transduced with CD4ζ CAR are capable of killing HIV-infected cells (FIG. 4A, CD8-CAR) and suppressing viral replication (FIG. 4B, CD8-CAR). Surprisingly, the CD4ζ CAR construct resulted in dramatically superior suppressive activity compared to the HIV-TCR construct, even when the CTL clone is matched.

Figure 5:
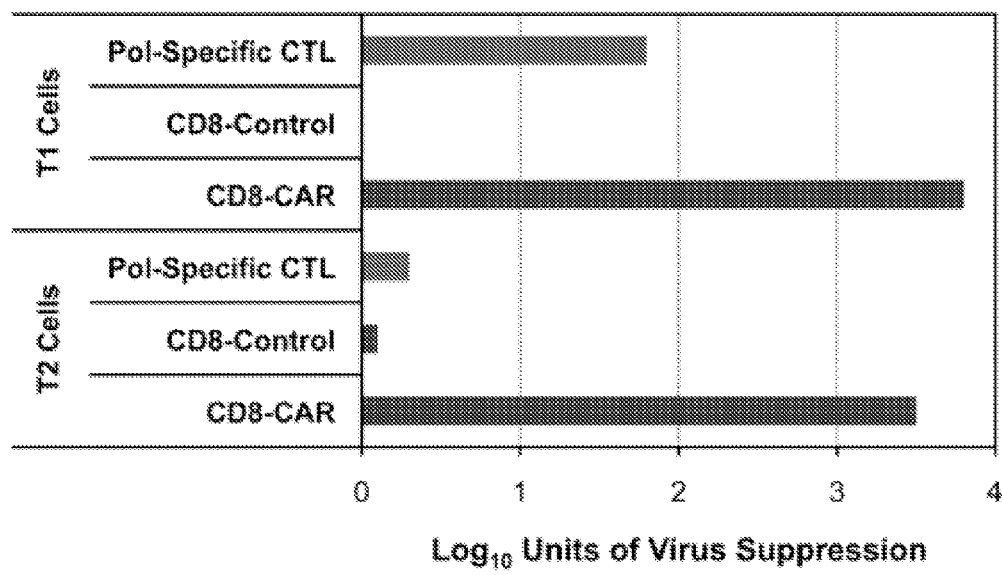
FIG. 5 is a graph showing HLA-I independence of CD4ζ transduced CD8+ T cell antiviral activity.

T1 cells or derivative T2 cells were infected with HIV-1 IIIB and co-cultured with CD8+ T cells transduced with the CD4ζ CAR construct or a primary HIV-I specific HLA-I restricted CD8+ T cell clone recognizing an epitope in reverse transcriptase (pol). Unlike the HIV-specific TCR cells of FIG. 2, the data in FIG. 5 shows that the killing and suppressive activity of the cells having the CD4ζ CAR construct is independent of HLA-I molecules. Thus, the methods and engineered cells according to the present invention are not HLA-restricted.

Figure 6:
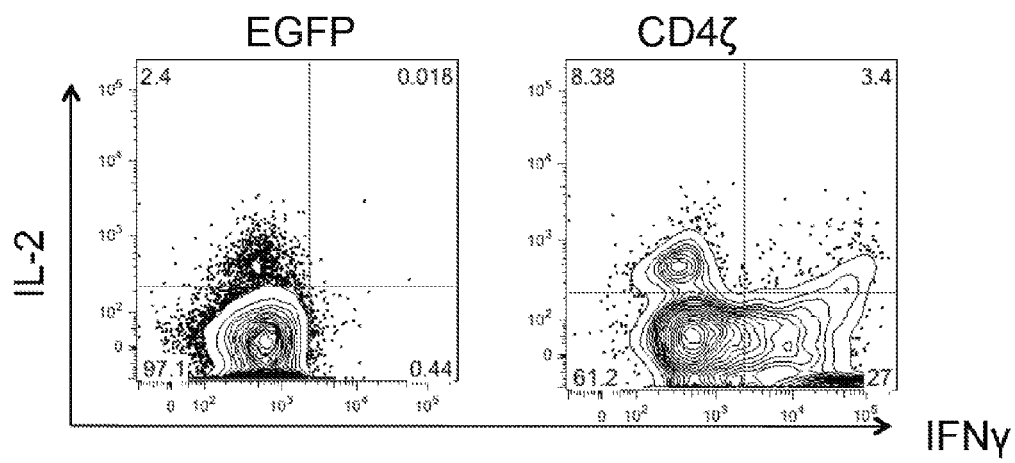
FIG. 6 are graphs showing HIV-1 specific cytokine production from CD4+ T cells via CD4 ζ.

CD4+ T cells were transduced with lentiviral vectors encoding either EGFP (EGFP, control) or EGFP-2A-CD4ζ (CD4 ζ). The cells were then incubated with HIV-1 infected T1 cells. Intracellular IL-2 and IFN-γ were analyzed by flow cytometry. The data in FIG. 6 shows that CARs can also function in CD4+ T-cells to act as HIV-1-specific helper cells.

Figure 7:
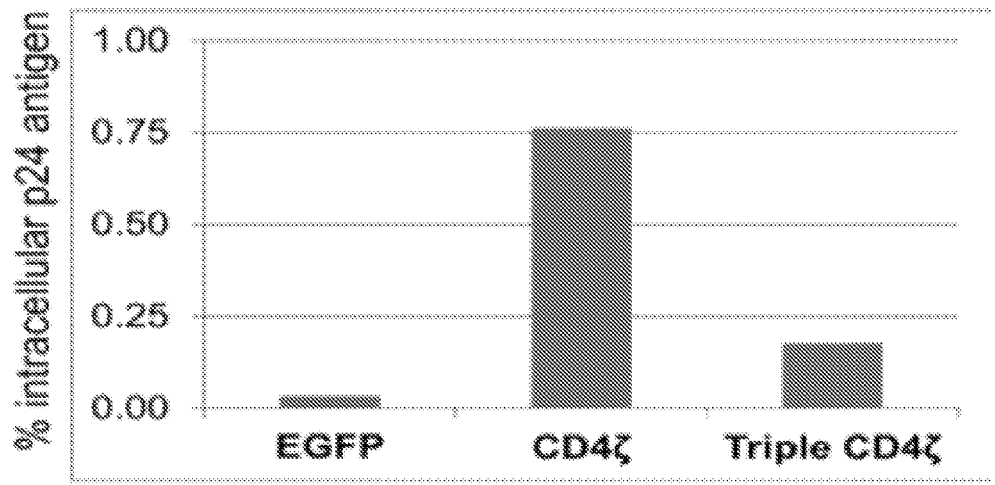
FIG. 7 is a graph showing the susceptibility of the cells transduced with the CD4ζ CAR construct and the Triple CD4ζ construct to HIV infection.

Unfortunately, it was found that CD8+ T-cells that express CD4 through transduction with CD4ζ CAR become susceptible to HIV infection. Specifically, as shown in FIG. 7, purified primary CD8+ T-cells were transduced with either CD4ζCAR (CD4ζ) or EGFP control vector (EGFP) and infected with R5-tropic HIV-1$_{JR-CSF}$ (JRCSF). The results demonstrate that CD8+ cells which were transduced with CD4ζ CAR are susceptible to HIV infection whereas CD8+ T-cells transduced with control vector were not significantly infected by HIV (EGFP).

Thus, to determine whether CD4ζ CAR could be combined with other anti-HIV reagents to confer protection from HIV infection, two shRNAs, one that downregulates CCR5 and one that downregulates HIV expression by targeting the LTR region, were introduced into the gene delivery vector containing CD4ζ CAR. The first shRNA, sh1005, inhibits R5-tropic HIV at the point of entry through downregulation of the CCR5 co-receptor. The second shRNA, sh516, directed to HIV itself, which unlike sh1005, has been found to be protective against both R5- and X4-tropic HIV.

Co-expression of sh1005 and sh516 in a single vector efficiently downregulates CCR5 expression and inhibits both X4- and R5-tropic HIV replication in PBMCs in vitro. No effects on cell viability, no up-regulation of interferon-inducible OAS1 expression in PBMCs, and no effects on colony forming cell (CFC) assay after transduction of FL-CD34+ cells were seen. Hematopoiesis in transplanted BLT mice was normal in marked cell populations. Most importantly, marked cells are protected from both R5 and X4 tropic HIV. Thus, in some embodiments, this base vector may be used to test expression and functionality of other CARs. For example, protection from R5 and X4 tropic HIV infection may be assessed by supernatant and intracellular gag p24 assays.

Figure 8:
FIG. 8 is a schematic representation of the protective CD4ζ CAR construct.

The sh1005/sh516 expression cassette was introduced into the EGFP-2A-CD4ζ vector. FIG. 8 schematically shows the CD4ζ CAR construct. This CAR construct having the sh1005, sh516, and CD4ζ (Triple CAR construct) allowed production of mature CD4+ and CD8+ T-cells but with a reduced percent engraftment (5-6% vs. 11%; not shown) compared to the original EGFP-2A-CD4ζ vector. The Triple CAR construct maintains ability to downregulate CCR5 and downregulate an HIV vector bearing mCherry as a reporter gene similar to sh1005/sh516 (data not shown). As shown in FIG. 7, using the Triple CAR construct, CD4ζ CAR successfully diminished HIV-1 susceptibility (Triple CD4ζ).

Therefore, in some embodiments, inhibitory RNAs known in the art may be similarly employed. Such inhibitory RNAs include those as disclosed in U.S. Pat. No. 7,737,124; U.S. Pat. No. 7,732,207; U.S. Pat. No. 7,195,916; and U.S. Pat. No. 7,919,309, which are herein incorporated by reference in their entirety. In some embodiments, other sequences such as the sequence encoding C46, a transmembrane fusion inhibitor, can be added or used in place of the shRNAs. It should be noted that other antiviral sequences may be used in place of or in addition to the shRNAs and C46 as described herein, and that selection of such antiviral sequences is within the skill of those in the art and may be based on the subject to be treated. Assays known in the art may be used to assess the activity of vectors and constructs according to the present invention. For example, the CFC assay can be used to determine the hematopoietic potential of CAR construct treated CD34+ HSPC compared to control vector and mock transduced cells in vitro by measuring total colony forming units (CFU) and various hematopoietic lineage types (erythroid, myeloid, and erythroid/myeloid) of CFU generated per condition. Briefly, transduced CD34+ cells are re-suspended in MethoCult H4034 and 500 cells plated per replicate. 12-14 days later, CFUs are scored under a microscope. Individual colonies can also be assessed for vector copy number by PCR; one may aim to maintain a copy number less than 3. Generally, no greater than 0.5-fold variation in total CFU and sub-type colonies compared to that of control vector or mock transduced conditions is desired.

Figure 9A:
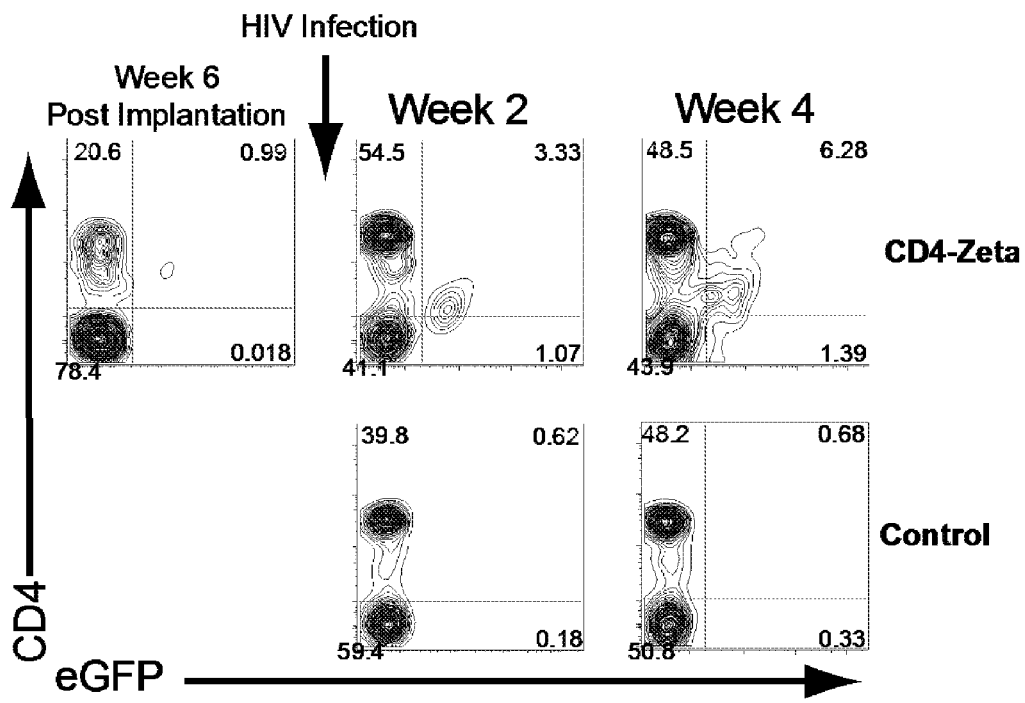
FIG. 9A is a graph showing the development of T cells from HSCs genetically modified with a CD4ζ CAR in humanized mice
Figure 9B:
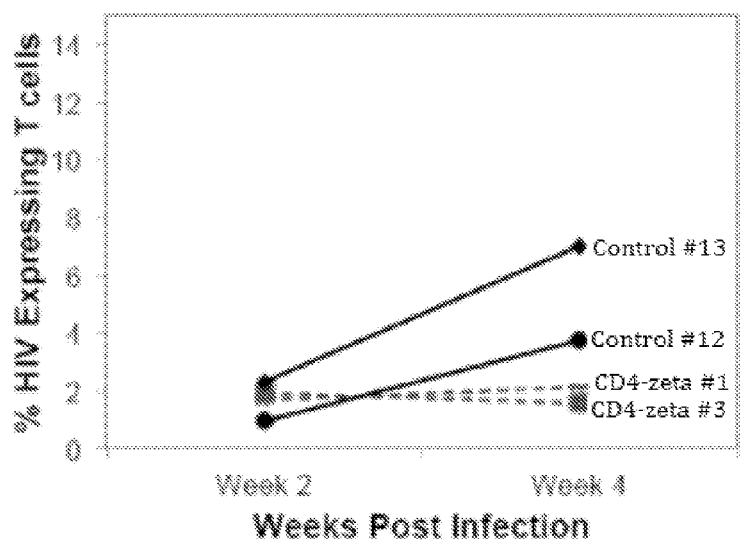
FIG. 9B is a graph showing the percent of HIV infected unmodified T cells and those expressing CD4ζ CAR.

To determine whether HSC transduced with a CAR would proceed successfully through thymopoiesis, HSCs modified with a lentiviral vector containing the CD4ζ CAR were transplanted into the humanized mouse model. Humanized mice were made with either CD4ζ CAR or left unmodified (control). As shown in FIG. 9A, peripheral blood of mature T-cells expressing the lentiviral vector marker gene (EGFP) and CD4ζ CAR were found to efficiently develop and expand following infection with HIV. In addition, as shown in FIG. 9B, HIV infection of T cells expressing CD4ζ CAR was suppressed as compared to the control.

CAR+C46 Construct

Figure 10:
FIG. 10 schematically represents the dual CD46-CD4ζ CAR lentiviral vectors (Double CAR constructs).

C46 is a peptide known to exhibit antiviral activity in non-human primates (NHPs). Thus, a lentiviral-based vector was developed to express a HIV-specific CAR along with the C46 fusion inhibitory antiviral peptide to determine whether the CAR construct prevents or inhibits infection of CAR-expressing effector cells in NHPs. A vector expressing both C46 and CD4ζ CAR as well as an eGFP reporter was generated to examine the antiviral effects during SHIV infection in the *M. nemestrina* model. Specifically, FIG. 10 schematically represents the CD46-CD4ζ CAR construct exemplified herein. The CAR construct has an FG-12-derived backbone. The inserts are central polypurine tract (cPPT); EF1α promoter (EF1α); C46; Ubiquitin C promoter (UbiC); EGFP-2A-CD4ζ CAR; and wPRE. EGFP fused with CD4ζ CAR with 2A peptide sequence serves as a transduction marker.

The ability of the lentiviral-based vector to transduce target cells and express the CAR and C46 molecules following modification of simian peripheral blood mononucleated cells (PBMCs) and HSCs may be screened using methods known in the art. The inhibition of SHIV infection and CAR-mediated polyfunctional responses in vector modified simian peripheral blood cells may be assayed using methods known in the art. Vectors expressing C46 and eGFP (without the CAR) or the CD4ζ CAR and eGFP (without C46) may be used as controls.

For example, to test the ability of newly synthesized lentiviral vectors, e.g., both single and double vectors containing C46 and/or the CAR, to effectively transduce and express in target cells, the respective vectors can be used to transduce simian PBMCs, in a limiting dilution fashion, following their stimulation with PHA and Interleukin-2 (IL-2). Vector expression may be determined by flow cytometry for eGFP and simian host cells and examined for expression of simian CD3, CD4, CD8. Vector expressing cells can be assessed for CAR CD4 expression by gating. In addition, C46 and CAR expression can be examined by Western blot using antibody probes for the respective proteins of transduced cell lysates. Transduction efficiencies and viral infectivity titers can be determined by limiting dilution analysis of vector expressing cells.

To determine the ability of these vectors to transduce and express in HSC and resultant progeny following their differentiation, simian HSC are transduced with C46 and/or CAR containing vectors at a multiplicity of infection (MOI) of 5-25 similar to that described by Trobridge, G., et al. (Blood 111, 5537-5543 (2008)). Cells will then be placed in methylcellulose and hematopoietic colony-forming activity is monitored. Resultant colonies are assessed for development into erythroid or myeloid/granulocyte lineages and vector expression is examined on individual colonies by flow cytometry for eGFP and CD4. Percentages of cells in each lineage are determined and any alteration in hematopoietic development is noted between untransduced, C46 and CAR-only transduced, and C46 and CAR dual vector (Double CAR C46 construct) transduced cells.

To confirm the protective antiviral effects of the C46 containing vector, groups of simian PBMCs are kept untransduced or transduced with either the C46 or CAR-only control vectors, or the Double CAR C46 construct following stimulation with PHA and IL-2. Three days following transduction, cells will then be exposed to infectious SHIV at a MOI of 1. Following virus exposure, cell culture supernatant is assessed for SHIV gag p27 production to monitor viral replication. A decreased or blocked SHIV replication in cultures containing cells that express the C46 molecule is expected.

The ability of the newly expressed CAR molecule to stimulate polyfunctional T cell responses in vitro in response to exposure to SHIV infected cells can be assayed using methods known in the art. Stimulated simian PBMCs are untransduced or transduced as described above with C46 or CAR-only control vectors, or the Double CAR C46 construct). Three days following transduction, cells are mixed with irradiated, syngeneic, previously SHIV-infected PBMCs. Following exposure, cells are assessed for expression of CD4, CD8 and interferon-gamma (IFN-γ), IL-2, tumor necrosis factor alpha, CD107a, and MIP-1β by flow cytometry. In addition, cytolytic activity is assessed in CAR-containing and control PBMC utilizing SHIV infected cells as target cells in a standard chromium-51 release assay. CAR ligation of HIV gp120 expressed on infected cells should induce T cell activation and confirm function of the receptor.

Triple Car Construct—In Vivo Studies

Human HSCs were transduced with the Triple CAR construct (sh1005/sh516/CD4ζ CAR, referred to herein as Triple CAR, Triple CD4ζ, or Triple CD4ζ CAR) and were transplanted into immunodeficient non-obese diabetic (NOD), severe combined immunodeficient (SCID), common gamma chain knockout (γc−/−) (NSG) mice containing human fetal liver and thymus tissue and assayed using methods known in the art. Specifically, CD34+ cells were purified from liver and transduced with lentiviruses containing the protective CD4ζ CAR and then transplanted into NSG mice with fetal liver stromal element and fetal thymus in matrigel. 3 weeks after transplantation, the transplant mice were sublethally irradiated (3 Gy), previously frozen CD34+ cells are thawed and transduced and injected into the mice where the cells engraft in the bone marrow. 6-12 weeks later, peripheral blood was collected and analyzed for human cell reconstitution and the mice were infected with HIV-1.

Following development of the transplanted tissue and genetically modified cells, vector-expressing cells in different organs were assessed. Cells were isolated and analyzed for their expression of human leucocytes GFP, CD4 and CCR5. Splenocytes from the CD4ζ CAR hu-BLT mice were analyzed by flow cytometry and gated on human CD45+ and CD4+GFP+ CD4ζ CAR expressing cells. These cells were accessed for surface marker such as T cells (CD5+), B cells (CD3-CD19+), macrophages/monocytes (CD14+) and NK cells (CD56+TCRab-CD337).

It was found that the CD4ζ CAR was expressed on a significant number of cells in the blood, spleen, thymus, and bone marrow of animals receiving vector modified HSCs, thereby indicating that these cells undergo hematopoiesis in the transplanted animals. Additionally, knockdown of CCR5 expression was observed in vector expressing cells in these animals, thereby indicating that the shRNA specific to CCR5 is functioning. Expression of the CD4ζ CAR construct on T cells, natural killer (NK) cells, B cells, and myeloid cells was observed in transplanted animals, thereby indicating that the genetically modified HSCs are capable of multilineage hematopoiesis in vivo.

Figure 11A:
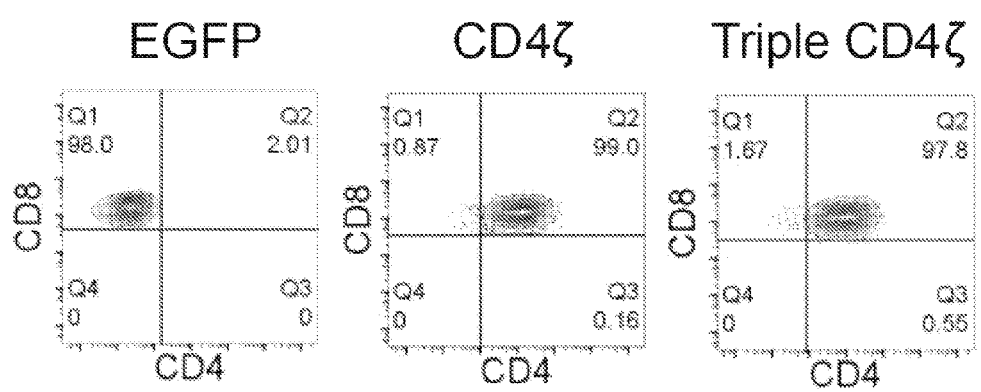
FIG. 11A shows CD8 cells purified from healthy donors and transduced with either GFP control vector, or CD4ζ CAR or the Triple CD4ζ CAR construct.
Figure 11B:
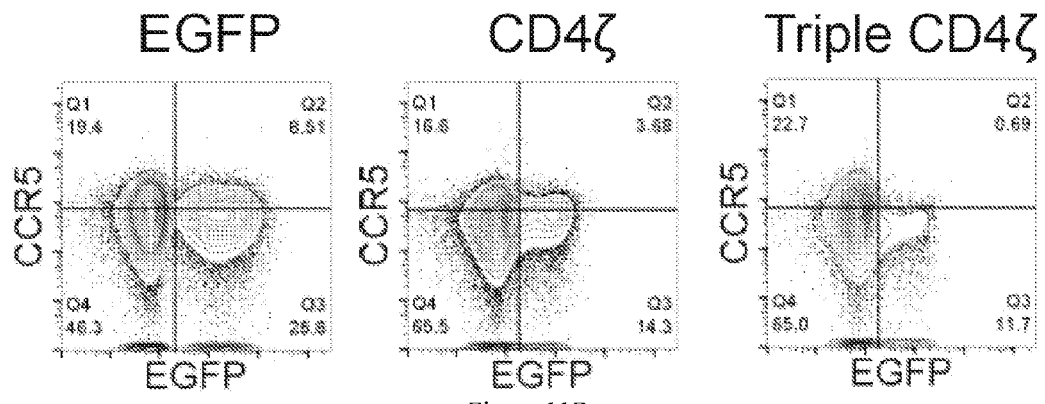
FIG. 11B shows CCR5 expression is down regulated by protective CD4ζ CAR compared to GFP or CD4ζ CAR control.

The transduction and expression of the CD4ζ CAR containing vector in sorted CD8+ T cells isolated from fresh peripheral blood mononuclear cells (PBMCs) was examined. Cells transduced with the Triple CAR construct were compared to cells transduced with a vector containing only the CD4ζ CAR or a vector containing only eGFP. As shown in FIG. 11A and FIG. 11B, transduction and expression of the vector(s) resulted in extracellular CD4 expression and CCR5 knockdown in cells expressing the Triple CAR Construct.

Figure 11C:
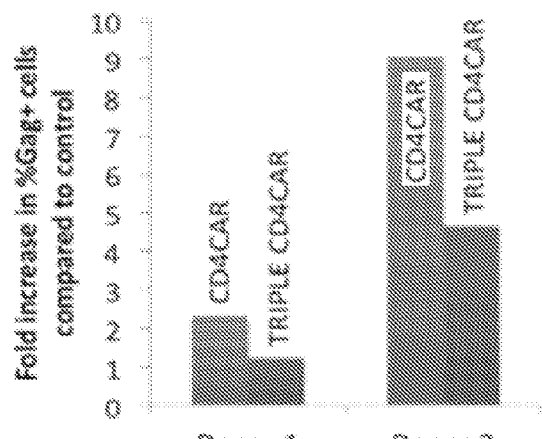
FIG. 11C shows the fold increase of HIV infection rate comparing HIV-1 exposed CD8 cells transduced with CD4ζ CAR or the Triple CD4ζ CAR construct to GFP control vector.
Figure 11D:
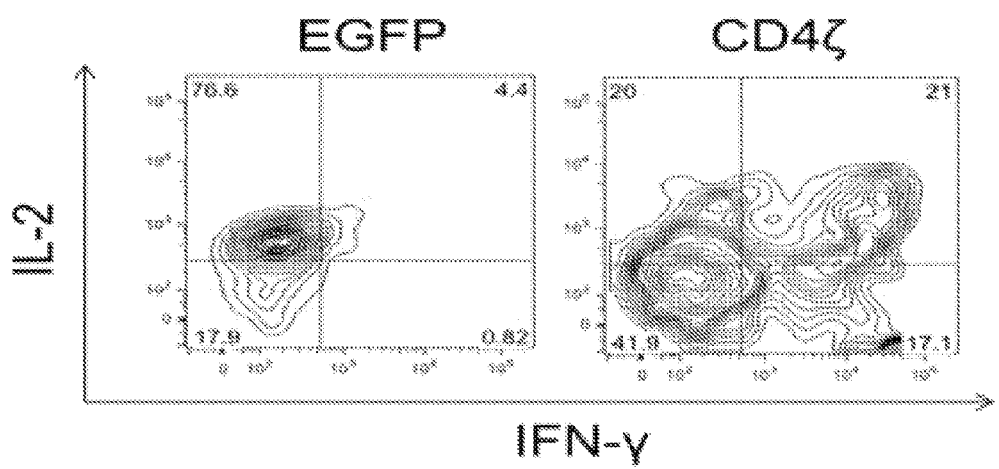
FIG. 11D shows cytokine production of GFP or Triple CD4ζ CAR transduced CD8 cells after stimulation with infected T2 cells.

As shown in FIG. 11C, the presence of the antiviral shRNAs protected the cells from infection. In addition, as shown in FIG. 11D, co-incubation of these cells with HIV-infected cells resulted in the induction of IL-2 and interferon-gamma (IFN-γ) compared to untransduced cells, thereby indicating that the CD4ζ CAR is functionally capable of inducing antiviral responses when expressed on CD8+ T cells. Thus, the Triple CAR construct protects transduced cells from HIV infection as well as expresses the CD4ζ CAR.

Figure 12A:
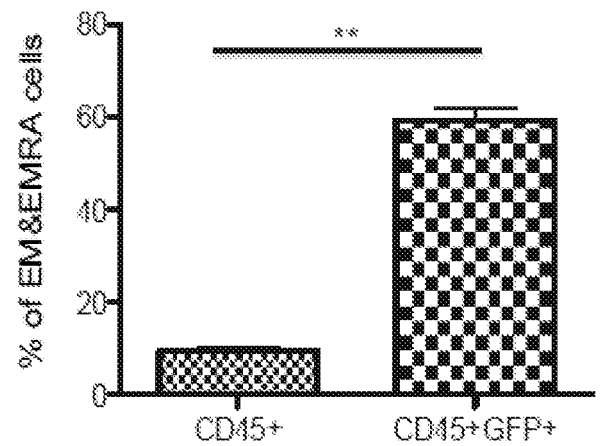
FIG. 12A is a graph summarizing the % EM&CM ratio among CD45+ and CD45+GFP+ CD4ζ CAR cells from infected CD4ζ CAR mice.
Figure 12B:
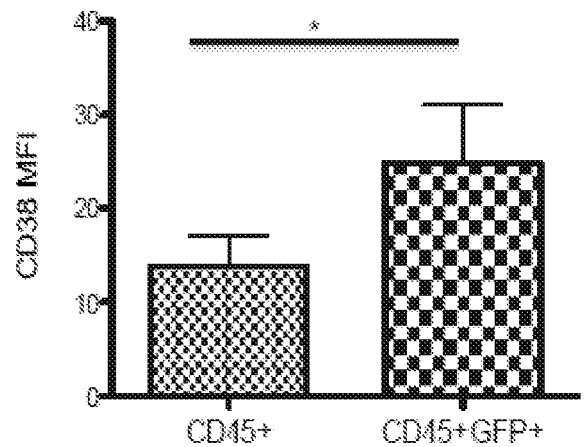
FIG. 12B is summarizes the CD38 mean fluorescence intensity (MFI) comparing CD45+ and CD45+GFP+ CD4ζ CAR cells from infected CD4ζ CAR mice.

In order to assess the functionality of the new CD4ζ CAR expressing cells, humanized mice transplanted with CD4ζ CAR cells were then infected with HIV for 5 weeks. After this infection time, virologic parameters and immune responses were assessed. Splenocytes from HIV-1 infected CD4ζ CAR mice were accessed for naïve (CD45RA+CD62L+), effector memory (EM) (CD45RA−CD62L−), central memory (CM) (CD45RA−CD62L+) and effector memory RA (EMRA) (CD45RA+CD62L−) development. Splenocytes from HIV-1 infected CD4ζ CAR mice were accessed for expression of activation marker CD38+. As shown in FIG. 12A, HIV infection resulted in the appearance of CD4ζ CAR expressing cells that possessed an effector phenotype (CD4+eGFP+CD27−CD45RA+/−) that is not represented in the non-CAR expressing cells. This was similar to the types of responses that were observed in studies examining HIV specific T cell responses utilizing a molecularly cloned TCR against HIV. In addition, as shown in FIG. 12B, these CD4ζ CAR expressing cells have greater levels of the CD38 activation molecule, thereby indicating the functional recruitment of these cells in antigen-specific T cell responses to HIV. Cells were then assessed for virus-specific activation of antiviral responses during HIV infection. Cells were removed from infected animals and were then cultured with a virally infected cell line or with uninfected cells. Shortly following exposure, CD4ζ CAR expressing cells produced INF-γ and TNF-α in response to HIV infected cells and did not respond to uninfected cells. These results show that CD4ζ CAR modified cells develop into effector phenotype and are activated after HIV infection and that cells carrying the CD4ζ CAR were primed in vivo to elicit HIV specific T cell responses following antigen encounter.

Figure 13A:
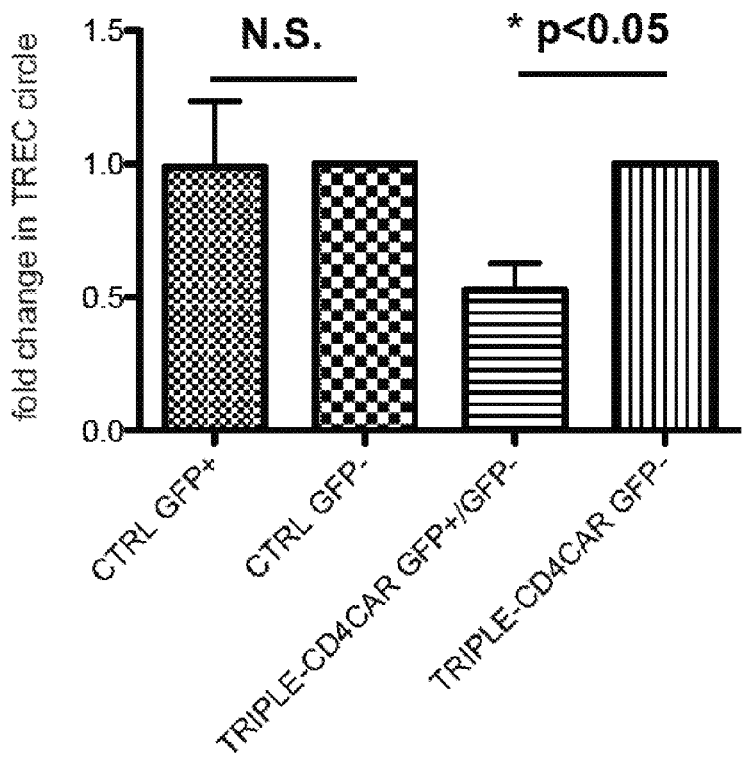
FIG. 13A is a graph showing a significant decrease in TREC levels in CD4ζ CAR expressing cells.
Figure 13B:
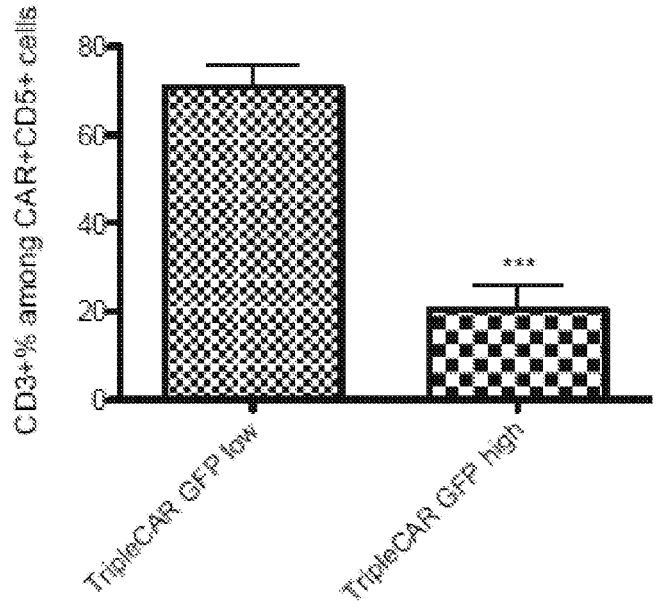
FIG. 13B is a graph showing CD3 expression on CD4ζ CAR expressing cells which was analyzed separately by high or low GFP expression.

Splenocytes from the CD4ζ mice were accessed and gated on CD4+GFP+ CD4ζ CAR expressing cells. Expression of CD3, CD5, CD7 and T cell receptor αβ were assessed and analyzed by flow cytometry. Thymocytes from the CD4ζ CAR mice and control GFP mice were assessed for their expression of CD5 and CD3 by flow cytometry. Thymocytes from the CD4ζ CAR and control mice were sorted based on CD5+ and GFP expression. DNA was purified from the sorted cells and TCR rearrangement excision circle (TREC) were measured by real time PCR. CD3 expression on CD4ζ CAR expressing cells was analyzed separately by high or low GFP expression. Interestingly, while the majority of cells that express the CD4ζ CAR vector that develop in vivo are T cells, as determined by expression of CD5, CD7, or CD2, there is a significant population of cells that lack cell surface CD3ε expression. Further phenotypic analysis of this population indicates that these cells have lower levels of endogenous TCRαβ receptor expression, which is necessary for cell surface expression of CD3. These cells from animals transplanted with human HSC modified with the CD4ζ CAR containing vector or a vector containing a deletion of the CD4ζ CAR solely expressing the eGFP marker protein were examined. A decrease in cell surface CD3ε expression in cells expressing the CD4ζ CAR/eGFP compared to cells expressing the eGFP control vector in the thymus of transplanted animals was observed. When these thymocytes were sorted and examined for the levels of T cell receptor excision circles (TRECs), as shown in FIG. 13A there was a significant decrease in TREC levels in CD4ζ CAR vector expressing cells compared to control vector expressing cells, thereby resulting in an approximately 50% decrease in TREC levels. This indicates that endogenous T cell receptor rearrangement is shut down as a result or CD4ζ CAR expression. FIG. 13B shows a reduction of CD3 expression on those cells expressing the greatest levels of the vector, thereby suggesting that higher levels of the CD4ζ CAR on the surface of these developing cells more effectively turns off endogenous TCR rearrangement. In summary, these data indicate that genetic modification of human HSCs with a CD4ζ CAR can result in multilineage hematopoiesis and the production of HIV specific T cells; a significant population of which that have their endogenous T cell receptor down regulated and solely express the CD4ζ CAR molecule.

Figure 14A:
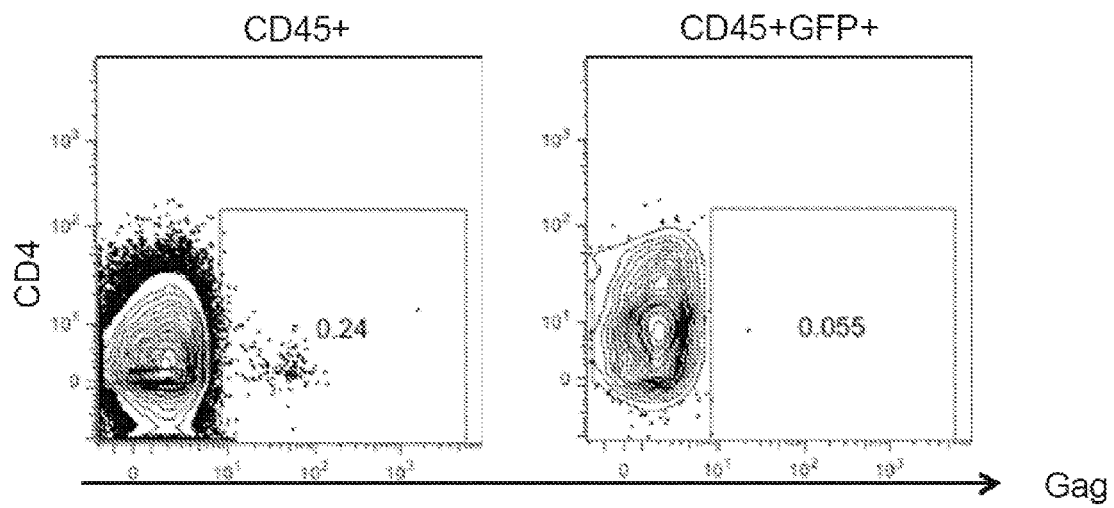
FIG. 14A and FIG. 14B are graphs showing the percentage of cells expressing the HIV p24Gag antigen.
Figure 14B:
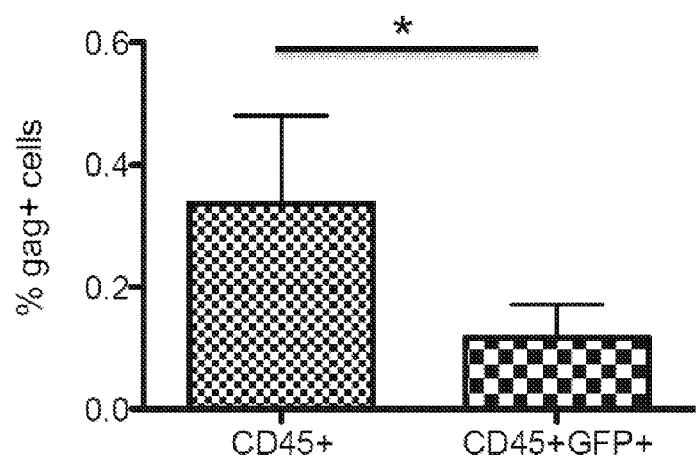

Mice were then examined for infection of CD4ζ CAR expressing cells by intracellular staining for HIV p24Gag antigen. Specifically, splenocytes from HIV-1 infected, CAR-transduced BLT mice were analyzed for intracellular gag expression among human CD45+ cells or CD45+GFP+ CD4ζ CAR cells. As shown in FIG. 14, significantly reduced levels of p24Gag expression were observed in cells expressing the Triple CAR Construct than in cells not expressing the construct. This indicates that these cells are protected from infection through the expression of the antiviral genes in the construct, allowing them to persist and respond against HIV in vivo.

Figure 15A:
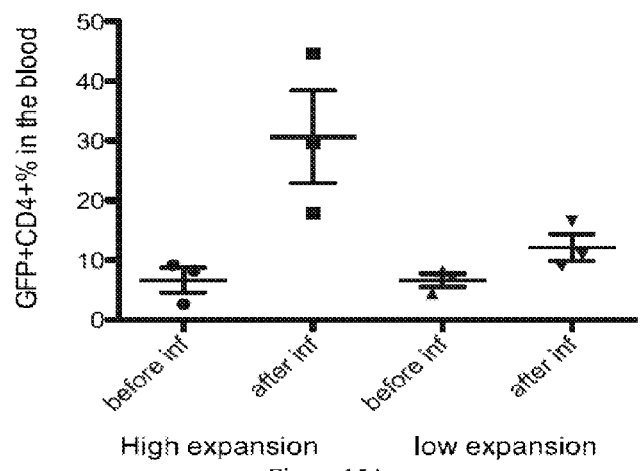
FIG. 15A shows the percentage of GFP+CD4+ CD4ζ CAR expressing cells in peripheral blood before and 5 weeks after infection.
Figure 15B:
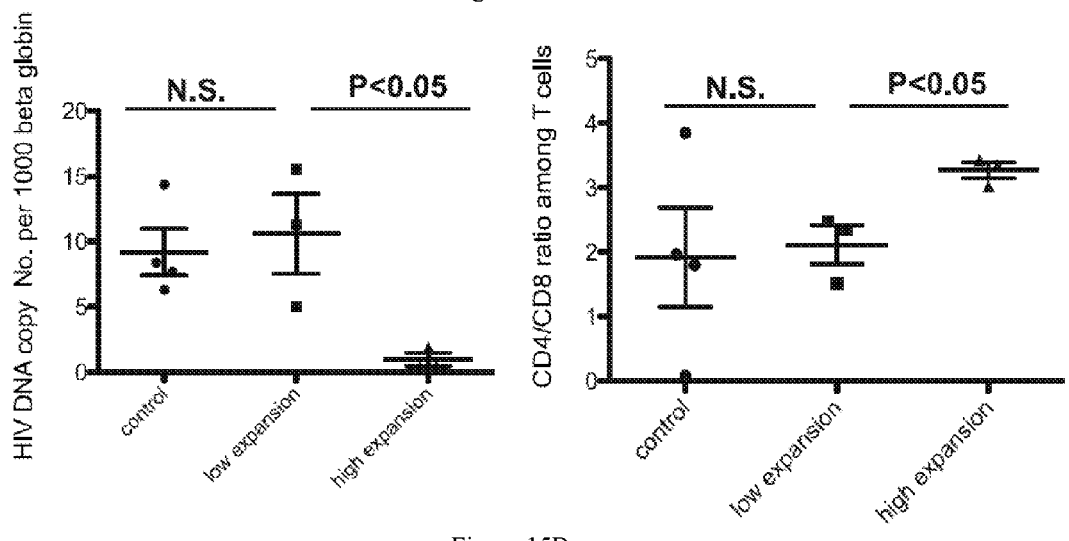
FIG. 15B shows the blood HIV DNA burden and CD4/CD8 ratio comparing control and CD4ζ CAR mice that are infected with HIV-1.
Figure 15C:
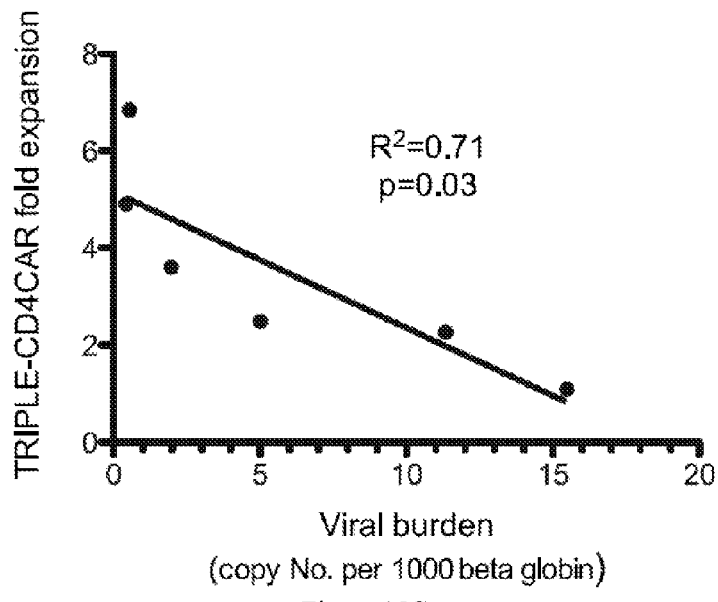
FIG. 15C shows the correlation of CD4ζ CAR expression cell expansion with viral burden in the peripheral blood.

HIV viral load was assessed in PBMCs and suppression of virus in mice receiving the Triple CAR Construct was observed. The percentage of GFP+CD4+ CD4ζ CAR expressing cells in peripheral blood before and 5 weeks after infection are accessed by flow cytometry. As shown in FIG. 15A, when mice reconstituted with different levels of CD4ζ CAR expressing cells were analyzed, mice that had a greater expansion of cells expressing the CD4ζ CAR vector (high expansion) had almost full suppression of HIV, whereas animals whose cells had lower levels of expansion did not have significant suppression of the virus. As shown in FIG. 15B, in addition to lower viral loads, a better preservation of CD4+ T cell ratios was observed in animals that had greater levels of cellular expansion of PBMC expressing the CD4ζ CAR vector. FIG. 15C shows that the levels of cellular expansion correlated with suppression of the virus. In summary, CD4ζ CAR cells successfully suppress HIV replication in vivo. Thus, in some embodiments, the present invention is directed to genetically modifying HSCs, HPCs, or HSPCs with a gene delivery vector containing a sequence encoding a CD4ζ CAR alone or in combination with one or more antiviral sequences such as a shRNA (e.g., sh1005 and/or sh516) to provide multilineage reconstitution of HIV-specific cells that are protected from HIV infection and/or lower viral loads in vivo following exposure to HIV.

Procedures

Human fetal tissue was purchased from Advanced Biosciences Resources or from StemExpress and was obtained without identifying information and did not require IRB approval for its use. Animal research described in this manuscript was performed under the written approval of the UCLA Animal Research Committee (ARC) in accordance to all federal, state, and local guidelines. Specifically, these studies were carried out under strict accordance to the guidelines in The Guide for the Care and Use of Laboratory Animals of the National Institutes of Health and the accreditation and guidelines of the Association for the Assessment and Accreditation of Laboratory Animal Care (AALAC) International under UCLA ARC Protocol Number 2010-038-02B. All surgeries were performed under ketamine/xylazine and isofluorane anesthesia and all efforts were made to minimize animal pain and discomfort.

1. Antibodies and Flow Cytometry

The following antibodies were used in flow cytometry: CD45, CD2, CD7, CD5, CD3, CD4, CD8, CD45RA, CD62L, CD38, CD19, CD14, CD337, CD56, TCRαβ (ebiosciences) and anti-HIV-1 core antigen clone KC57 (Beckman Coulter). Cell surface markers are conjugated to either FITC, PE, PerCP-Cy5.5, PE-Cy5, PE-Cy7, EVD, APC, APC-eflou780, alexa700, eflour405, Pacific orange or pacific blue in appropriate combination. The cells were acquired using LSRFortessa flow cytometer (BD biosciences) and FACSDiva software. Data were analyzed using FlowJo software.

2. Lentiviral Vector Production

The Lentivirus GFP control vector, the CD4ζ CAR Construct, and the Triple CD4ζ CAR Construct were produced in 293FT cells using the Invitrogen ViraPower Lentiviral Expression system with pCMV.ΔR8.2.Δvpr packaging plasmid and the pCMV-VSV-G envelope protein plasmid as previously described (D. M. Brainard et al., *J. Virol.* 83, 7305-7321 (2009)).

4. Quantitation of TCR Rearrangement Excision Circles

Thymocytes from CD4 ζCAR or GFP vector modified mice were sorted on a FACSaria based on their expression of GFP and CD5. DNA was extracted from sorted cells using phenol/chloroform. Real time PCR was used to qualified TREC expression level normalized to β-globin. Oligos, probes and condition are described previously (Douek et al., Lancet 355, 1875-1881 (2000)).

Novel Car Production

As used herein, "CAR constructs" refers to nucleic acid molecules which comprise CD4, preferably human CD4, fused to the signaling domain of the CD3 complex ζ-chain. CAR constructs include truncated CAR constructs, Double CAR constructs, and Triple CAR constructs. As used herein, "truncated CAR constructs" refers to nucleic acid molecules which comprise a truncated CD4 (e.g., comprising only D1, D1+D2, or D1+D2+D3 of CD4, preferably human CD4), fused to the signaling domain of the CD3 complex ζ-chain. Truncated CAR constructs include truncated Double CAR constructs, and truncated Triple CAR constructs. As used herein, "Double CAR constructs" refers to nucleic acid molecules which comprise CD4, preferably human CD4, fused to the signaling domain of the CD3 complex ζ-chain and one antiviral sequence. As used herein, "Triple CAR constructs" refers to nucleic acid molecules which comprise CD4, preferably human CD4, fused to the signaling domain of the CD3 complex ζ-chain and two antiviral sequences. As used herein, "truncated Double CAR constructs" refers to nucleic acid molecules which comprise a truncated CD4 (e.g., comprising only D1, D1+D2, or D1+D2+D3 of CD4, preferably human CD4), fused to the signaling domain of the CD3 complex ζ-chain and one antiviral sequence. As used herein, "truncated Triple CAR constructs" refers to nucleic acid molecules which comprise a truncated CD4 (e.g., comprising only D1, D1+D2, or D1+D2+D3 of CD4, preferably human CD4), fused to the signaling domain of the CD3 complex ζ-chain and two antiviral sequences. The CAR constructs may further include one or more of the following sequences: a viral promoter for binding regulator proteins (e.g., 5' long terminal repeat (LTR)), one or more antiviral sequences (e.g. sh1005, sh516, C46), a sequence that helps regulate transcription (e.g., 7SK), a gene promoter (e.g., Ubiquitin C promoter (UbC)), a reporter gene (e.g., enhanced green fluorescent protein (EGFP)), and other transcription and expression sequences such as H1, 2A, poly purine tract (cPPT), elongation factor 1 alpha (EF1 α), woodchuck hepatitis post-transcriptional regulatory element (wPRE), and ΔLTR. Examples of CAR constructs according to the present invention include CD4ζ CAR, Double CAR C46, Triple CD4ζ CAR, CD4D1D2D3CAR, CD4D1D2CAR, CD4D1CAR, and second generation CAR constructs.

CAR constructs according to the present invention may be produced by genetic swapping of the gp120-binding domain and/or signaling domain in the prototype CD4ζ CAR construct. See FIG. 8. One may produce additional CARs with improved functionality. For example, second generation CAR constructs are produced by swapping the CD4 domain with Env-binding single-chain broadly neutralizing antibodies; this single-chain antibody approach was shown to function in parallel with the CD4ζ CAR in early studies and is the standard CAR approach used for targeting cancer. The genes for several broadly neutralizing antibodies including b12, X5, 2G12, 4E10, and VRC01 may be used. Single chain versions can be produced through standard methodology, introducing a flexible linker between the heavy and light chains. Binding of single chain antibodies to HIV is compared to the parental antibodies by standard methods. In addition, truncation and mutation of the CD4 component of CAR according to the present invention may be produced to eliminate binding with other natural ligands of CD4 receptor, such as IL-16 and MHCII, to reduce potential nonspecific activation of the CD4ζ CAR. Each of these novel receptors can be produced in two versions: one with the CD3ζ chain signaling domain, and another with a fusion of the CD3ζ chain and the CD28 signaling domain. This "second generation CAR" strategy may improve the survival and proliferation of CAR-transduced T-cells by providing a co-stimulatory "second signal" in addition to the primary T-cell receptor signal.

Vectors containing second generation single-chain antibody CARs, in versions with either the CD28 or 4-1BB signaling domains in tandem with the CD3 ζ chain were modified to allow convenient replacement of the single-chain domains with new single-chain genes. In brief, a portion including the Xba I-Sma I restriction sites (starting just upstream of the single-chain antibody and ending within the hinge region) was modified in a secondary vector (pUC19) by point mutagenesis (QuikChange, Invitrogen) to create an Apa I site in the hinge region through silent mutations. After confirmation of the correct sequence, the Xba I-Sma I restriction fragment was swapped into the vectors (also including a first generation version with only the CD3 ζ chain).

Figure 16:
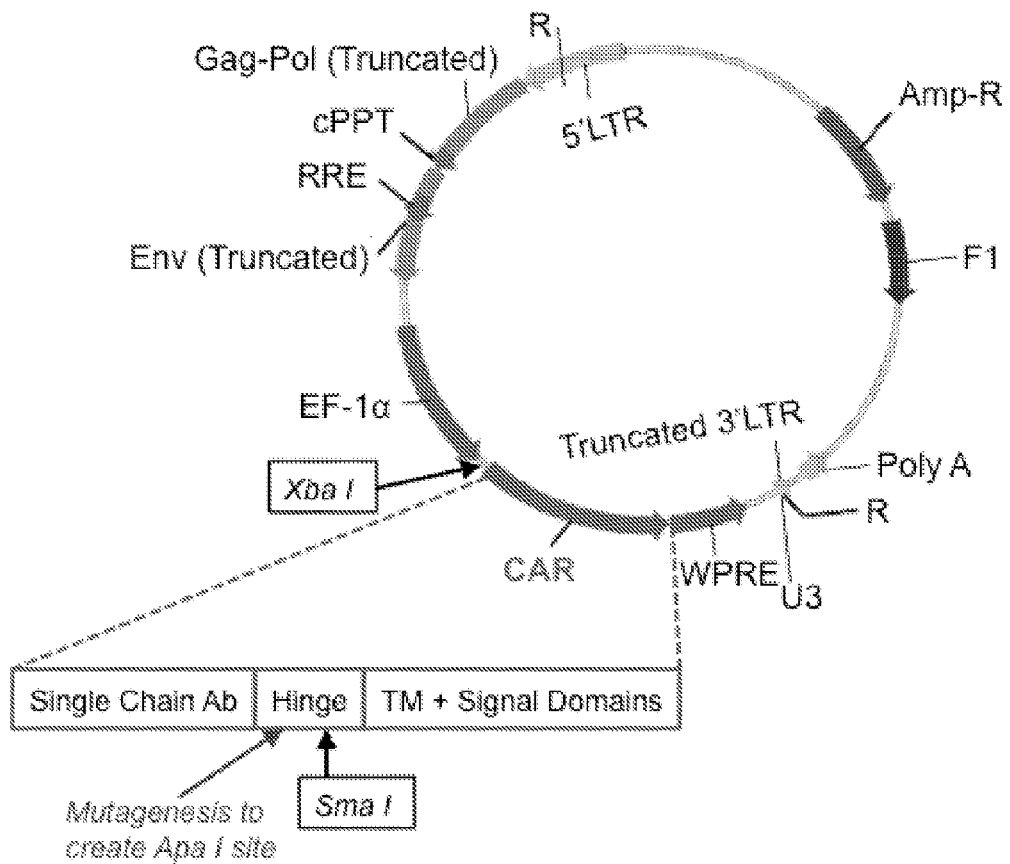
FIG. 16 schematically shows CAR vector modification and strategy to develop CAR constructs according to the present invention.

FIG. 16 schematically shows the CAR vector modification and strategy to develop CAR constructs according to the present invention. A map of a CAR construct is shown. Within the Xba I-Sma I fragment, a silent mutation was introduced in the Hinge region to introduce an Apa I site (GGCCCT→GGGCCC (SEQ ID NO:1)), and this fragment was re-introduced into the vector. One plasmid was generated for each version with different signaling domains (CD28-ζ, 4-1BB-ζ, and ζ). New CARs were generated by synthesizing the single chain antibody and partial hinge sequence including the Xba I and Apa I sites, and using those enzymes to cut and ligate the new constructs into the vector.

Using the three vectors described above (signaling domains: ζ, CD28-ζ, and 4-1BB-ζ) novel single chain antibodies designed from sequences of 7 well-defined broadly neutralizing antibodies (Table 1) were inserted. Thus, in some embodiments, second generation CAR constructs according to the present invention comprises a sequence which encodes one of the single chain antibody sequences set forth in Table 1 as follows:

The Xba I-Apa I inserts were custom synthesized (GeneArt) as concatenated heavy chain variable region with linker (GGGGSGGGGSGGGGS (SEQ ID NO:16)) with light chain variable region, and then swapped into the three vectors. These 21 CAR constructs may be used to generate gene delivery vectors to be used in accordance with the present invention, for example, to transduce cells, e.g., stem cells, CD8+ T lymphocytes, etc., for functional testing.

Figure 17:
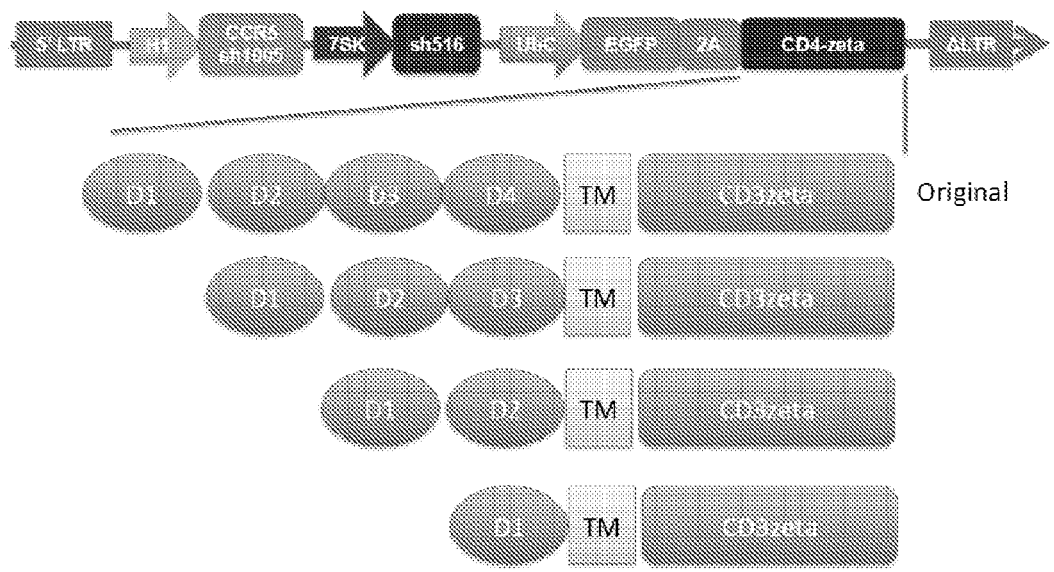
FIG. 17 schematically shows the various truncation mutants that have been made. As shown, from top to bottom, the CD4ζ constructs are: CD4ζ CAR, CD4D1D2D3CAR, CD4D1D2CAR, and CD4D1CAR.
Figure 18:
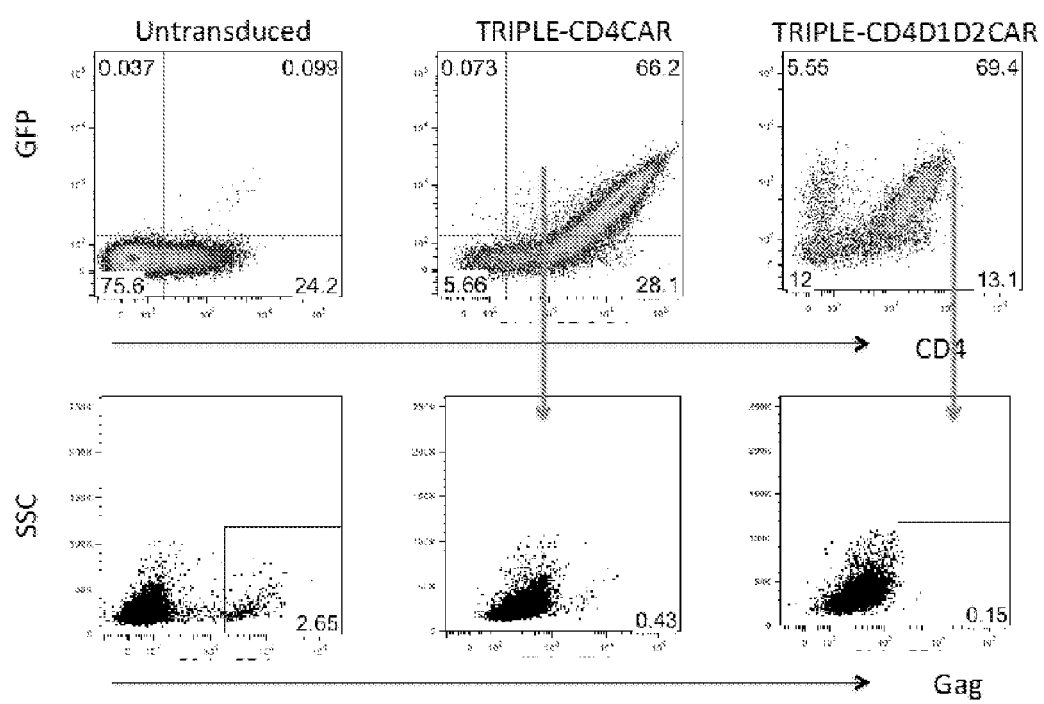
FIG. 18 are graphs showing that Triple CD4D1D2CAR is even more resistant to HIV infection than Triple CD4ζ CAR. Jurkat cells were transduced and then infected with NL4-3 for 3 days.

Truncation of CD4ζ CAR is generated by mutagenesis PCR of the original CAR construct sequentially deleting CD4 D4 domain, D3-D4 domains, D2-D4 domains. Mutagenesis on the CD4 D1 domain may also be generated using mutagenesis PCR. FIG. 17 depicts the various truncation mutants that have been made. FIG. 18 demonstrates how a truncation mutant containing the D1 and D2 domains of CD4, described in FIG. 17, can reduce the ability of this CAR to allow HIV infection in the context of other protective genes, which include a CCR5-specific shRNA and HIV-LTR specific shRNA. These CAR constructs may be used to generate gene delivery vector to reduce binding of

TABLE 1

| Antibody | Specificity | | Sequence |
| --- | --- | --- | --- |
| VRC01 | CD4BS | VL | EIVLTQSPGTLSLSPGETAIISCRTSQYGSLAWYQQRPGQAPRLVIYSGSTRAAGIP<br>DRFSGSRWGPDYNLTISNLESGDFGVYYCQQYEFFGQGTKVQVDIKR<br>(SEQ ID NO: 2) |
| | | VH | MLLLVTSLLLCELPHPAFLLIPQVQLVQSGGQMKKPGESMRISCRASGYEFIDCTLN<br>WIRLAPGKRPEWMGWLKPRGGAVNYARPLQGRVTMTRDVYSDTAFLELRSLTVDDTA<br>VYFCTRGKNCDYNWDFEHWGRGTPVIVSS (SEQ ID NO: 3) |
| X5 | CD4i | VL | ELVLTQSPGTLSLSAGERATLSCRASQSVSSGSLAWYQQKPGQAPRLLIYGASTRAT<br>GIPDRFSGSGSGTDFTLTIGRLEPEDLAVYYCQQYGTSPYTFGQGTKLEI<br>(SEQ ID NO: 4) |
| | | VH | MLLLVTSLLLCELPHPAFLLIPLEQSGAEVKKPGSSVQVSCKASGGTFSMYGFNWVR<br>QAPGHGLEWMGGIIPIFGTSNYAQKFRGRVTFTADQATSTAYMELTNLRSDDTAVYY<br>CARDFGPDWEDGDSYDGSGRGFFDFWGQGTLVTVSS (SEQ ID NO: 5) |
| PGT126 | N-Glycan | VL | QSALTQPPSASGSPGQSISISCTGTSNRFVSWYQQHPGKAPKLVIYGVNKRPSGVPD<br>RFSGSKSGNTASLTVSGLQTDDEAVYYCSSLVGNWDVIFGGGTKLTVL<br>(SEQ ID NO: 6) |
| | | VH | MLLLVTSLLLCELPHPAFLLIPQPQLQESGPGLVEASETLSLTCTVSGDSTAACDYF<br>WGWVRQPPGKGLEWIGGLSHCAGYYNTGWTYHNPSLKSRLTISLDTPKNQVFLKLNS<br>VTAADTAIYYCARFDGEVLVYHDWPKPAWVDLWGRGTLVTVTSS<br>(SEQ ID NO: 7) |
| PGT128 | N-Glycan | VL | QSALTQPPSASGSPGQSITISCTGTSNNFVSWYQQHAGKAPKLVIYDVNKRPSGVPD<br>RFSGSKSGNTASLTVSGLQTDDEAVYYCGSLVGNWDVIFGGGTKLTVL<br>(SEQ ID NO: 8) |
| | | VH | MLLLVTSLLLCELPHPAFLLIPQPQLQESGPTLVEASETLSLTCAVSGDSTAACNSF<br>WGWVRQPPGKGLEWVGSLSHCASYWNRGWTYHNPSLKSRLTLALDTPKNLVFLKLNS<br>VTAADTATYYCARFGGEVLRYTDWPKPAWVDLWGRGTLVTVSS (SEQ ID NO: 9) |
| PG9 | V2 | VL | QSALTQPASVSGSPGQSITISCNGTSNDVGGYESVSWYQQHPGKAPKVVIYDVSKRP<br>SGVSNRFSGSKSGNTASLTISGLQAEDEGDYYCKSLTSTRRRVFGTGTKLTVL<br>(SEQ ID NO: 10) |
| | | VH | MLLLVTSLLLCELPHPAFLLIPQRLVESGGGVVQPGSSLRLSCAASGFDFSRQGMHW<br>VRQAPGQGLEWVAFIKYDGSEKYHADSVWGRLSISRDNSKDTLYLQMNSLRVEDTAT<br>YFCVREAGGPDYRNGYNYYDFYDGYYNYHYMDVWGKGTTVTVSS<br>(SEQ ID NO: 11) |
| 10E8 | MPER | VL | SYELTQETGVSVALGRTVTITCRGDSLRSHYASWYQKKPGQAPILLFYGKNNRPSGV<br>PDRFSGSASGNRASLTISGAQAEDDAEYYCSSRDKSGSRLSVFGGGTKLTVL<br>(SEQ ID NO: 12) |
| | | VH | MLLLVTSLLLCELPHPAFLLIPEVQLVESGGGLVKPGGSLRLSCSASGFDFDNAWMT<br>WVRQFPGKGLEWVGRITGPGEGWSVDYAAPVEGRFTISRLNSINFLYLEMNNLRMED<br>SGLYFCARTGKYYDFWSGYPPGEEYFQDWGRGTLVTVSS (SEQ ID NO: 13) |
| 3BNC117 | CD4BS | VL | DIQMTQSPSSLSASVGDTVTITCQANGYLNWYQQRRGKAPKLLIYDGSKLERGVPSR<br>FSGRRWGQEYNLTINNLQPEDIATYFCQVYEFVVPGTRLDLKRTVAAP<br>(SEQ ID NO: 14) |
| | | VH | MLLLVTSLLLCELPHPAFLLIPQVQLLQSGAAVTKPGASVRVSCEASGYNIRDYFIH<br>WWRQAPGQGLQWVGWINPKTGQPNNPRQFQGRVSLTRHASWDFDTFSFYMDLKALRS<br>DDTAVYFCARQRSDYWDFDVWGSGTQVTVSSASTKGP (SEQ ID NO: 15) | the CD4 component to MHCII. These CAR constructs may be used to generate gene delivery vectors to be used in accordance with the present invention as stated above.

Additional Examples

Selection of Stem Cell Type

CD34+ hematopoietic stem cells have been shown to fully reconstitute the hematopoietic lineage. Human HSPC can fully reconstitute human B-cell, T-cell, NK and myeloid lineages in an advanced humanized mouse model (bone marrow, fetal liver, fetal thymus-BLT mouse). The introduction of HIV-specific CARs into HSPC allows differentiation of these cells in vivo into both CD4 and CD8 mature T-cell types expressing the receptor. As disclosed herein, the surrogate humanized bone marrow, fetal liver and thymus (BLT) mouse model was in initial experiments to demonstrate that human CD34+ HSPCs can be genetically modified with a lentiviral vector containing a molecularly cloned TCR specific to HIV, and subsequently develop into mature, fully functional CTL. Importantly these mature effector cells do not require any particular HLA molecule to attack target cells.

Memory T-cells have heterogeneous phenotypes, including central memory T ($T_{CM}$) cells and effector memory T ($T_{EM}$) cells. A new population of stem cell memory T ($T_{SCM}$) cells have been identified and exhibit stem-cell-like qualities of self-renewal and multipotent differentiation to memory and effector T-cell subsets. Human $T_{SCM}$ cells are a memory T-cell subset, but with a distinct phenotype and gene expression profile from $T_{CM}$ and $T_{EM}$. They can be clonally expanded after antigenic stimulation, with enhanced abilities to proliferate and reconstitute and, importantly, can be serially transplanted in immunodeficient mice. These cells are multi-potent in generating $T_{CM}$ and $T_{EM}$ cells subsets in vitro. Thus, these cells exhibit a stem-cell-like behavior, consistent with properties of mouse $T_{SCM}$ cells that show enhanced self-renewal and multi-potency in serial transplantation experiments. Because of the long-term self-renewal properties and multi-potent differentiation properties, the $T_{SCM}$ are ideal for genetic engineering of T-cell effector activities. Using the methodology of Gattinoni, et al., the in vitro propagation of $T_{SCM}$ cells (CD8+/CD45RA+/CD45RO−/CCR7+/CD62L+/CD95+/CD58+). 67% of $T_{SCM}$ differentiated to other subtypes including $T_{EM}$ (CD8+/CD45RA−/CD45RO+/CCR7−/CD62L−) and $T_{C}M$ (CD8+/CD45RA−/CD45RO+/CCR7+/CD62L+) subsets was achieved (data not shown).

$T_{SCM}$ represent a population of T-cells that do not require thymic development and transgene expression is limited to T-cell lineages only. The derivation of $T_{SCM}$ cells can be verified using methods known in the art. For example, CD45RA+ naïve T-cells are positively isolated from human peripheral blood and stimulated with anti-CD3/CD28 antibodies in the presence of GSK-3β inhibitor, TWS119, to inhibit T-cell differentiation and IL-2 for 14 days. $T_{SCM}$ cells may be induced in about 5% of either CD4+ or CD8+ T-cells. $T_{SCM}$ population can be expanded from naïve precursors in the presence of low doses of IL-7 and IL-15 (5 ng/ml each) following anti-CD3/CD28 antibodies stimulation. If desired, one can compare both protocols for expansion of gene modified $T_{SCM}$ cells. CD45RA and CD62L naïve T-cells are FACS-sorted and stimulated with anti-CD3/CD28 antibodies in the presence (condition A) or absence (condition B) of IL-2 and TWS119 for 2 days. Cells are then transduced with DC CARs and cultured in the presence of either: IL-2 and TWS119 (condition A); or IL-7 and IL-15 (condition B) for 12 days. The function of transduced $T_{SCM}$ can be characterized after differentiation to $T_{EM}$ cells, e.g., with anti-CD3/CD28 antibodies for 6 days and CTL, cytokine production, and proliferative activity against HIV using methods known in the art.

The ability of $T_{SCM}$ propagated in vitro to kill HIV infected cells was tested using a standard CTL chromium release assay (Yang O. Methods in Molecular Biology. 2009; 485:407-15). The results summarized in Table 1 show that T2 cells infected with HIV were killed by $T_{SCM}$ transduced with CD4ζ CAR (Triple CAR) at a significantly greater level than $T_{SCM}$ cells not transduced or transduced with EGFP control vector.

TABLE 2

| CD4ζ Specific HIV-1 Infected Cell Killing | | |
|---|---|---|
| | Uninfected | HIV-1 Infected |
| Untransduced | 3.48 ± 0.22% | 2.80 ± 0.01% |
| EGFP | 1.04 ± 0.09% | 1.78 ± 0.20% |
| Triple CAR | 4.30 ± 0.03% | 28.20 ± 2.56% |

T2 cells infected with or without HIV-1 NL4-3 (M20A) labeled with Na$_2$ ($^{51}$CrO$_4$) and incubated for 3.5 hours with Tscm transduced with or without Triple CAR at a 10:1 ratio. Cytolytic activity determined by analysis of chromium release.

CD4ζ CAR transduced CD4+ and CD8+ $T_{SCM}$ cells also respond to HIV-1 infected cells by producing IL-2 and IFN-γ (data not shown).

If CAR expression on non-T-cells is undesired, the CAR constructs may be modified for T-cell specific expression, e.g., contain a CD3 δ promoter in place of the ubiquitin C promoter (see FIG. 8).

Engraftment and Differentiation of HSPCs and TSCM Transduced with CARS in Humanized BLT Mice The in vivo repopulation of T-cells derived from HSPC and $T_{SCM}$ cells may be assayed using methods known in the art. For example, for $T_{SCM}$ derivation, T-cells are isolated from the spleen, thymic organoid, and/or peripheral blood of BLT mice and $T_{SCM}$ cells are cultured as previously described. After stimulation with anti-CD3/CD28 antibodies for two days, the cells are transduced with the CAR-containing vector marked with EGFP or, separately, with a control vector containing only EGFP and then cultured for a further 12 days. CD34+ HSPCs from fetal liver is also transduced with the CAR-containing vector or, separately, is transduced with a control vector containing only EGFP. One million of CAR vector-transduced cells or control vector containing cells from HSPCs and $T_{SCM}$ cells are separately infused intravenously into irradiated BLT mice. 6-8 weeks post-transplantation for mice receiving HSPC or $T_{SCM}$ cells, one may begin analyzing peripheral blood for EGFP expression and cellular lineage marker expression on CD3+CD4+ and CD3+CD8+ T-cells, CD19+ B-cells, CD3−CD56+ NK cells, CD14+ monocytes, CD11c+ dendritic cells every two weeks for 18 weeks (24 weeks post-transplant) to determine the maintenance of transduced cells.

CAR vector expression can also be assessed using flow cytometry or sorting EGFP+ cells and then performing a Western Blot for the CAR protein of interest. Antiviral shRNA gene expression can be assessed in developing cells and in vector expressing cells by quantitative reverse transcriptase PCR (qRT-PCR) specific for the shRNA sequences. In addition, one may quantitate absolute cell counts in peripheral blood samples from the treated subjects for each cell subset using assay methods known in the art. One may also assess the effects on the endogenous TCR repertoire to monitor for skewing of T-cell development by spectratyping EGFP+ sorted T-cells. Any alterations in hematopoietic development in vector-modified cells versus unmodified cells may be noted and further evaluated.

Anti-HIV Activity and Generation of Functional Immune Responses

Antiviral efficacy and immune function can be assessed in BLT mice containing CAR vector-modified and unmodified cells derived from HSPCs, and $T_{SCM}$ cells. For example, mice containing either vector modified cells or control EGFP vector modified cells are assessed following infection with HIV (200 ng p24) or in uninfected animals. Cellular phenotype, particularly CD3+CD4+ and CD3+CD8+ cell ratios, and HIV gag p24 expression is assessed every two weeks following infection by flow cytometry. Differentiation of vector-modified cells into $T_{EM}$ phenotype is monitored using methods known in the art. Plasma viral RNA is monitored by qRT-PCR for HIV sequences. HIV infection in CD4+ T-cells and in CAR vector expressing cells are assessed following sorting the EGFP+ population and qPCR for HIV sequences. Viral mutation and potential immune escape are monitored in plasma viral RNA by direct sequencing. At sequential times, groups of mice are assessed for these parameters in the spleen, bone marrow, human thymus, lymph nodes, and gut for cellular phenotype and virologic factors.

Effect of CARs on Viral Reservoir

A latent reservoir has been established in BLT mice (Marsden M, Kovochich M, Suree N, et al. Journal of Virology. 2012; 86(1):339-47). Preliminary data suggest that peripheral blood T-cells transduced with genes encoding the anti-gag TCR can kill latently infected cells induced to produce virus by addition of PKC activators (not shown). Consequently, CAR-expressing cells may be able to similarly eliminate activated reservoir cells. One may assess the ability of T-cells from BLT mice expressing CARs to kill reservoir cells ex vivo, using activated latently infected U1 cells as targets. One may obtain splenocytes from infected animals receiving CAR-transduced HSPC and control animals, and determine levels of activation-inducible (i.e., latent) infection by subjecting splenocytes to co-stimulation followed by analysis of intracellular gag p24 expression. Quantitation of relative latent infection levels can also be achieved using HIV-1 RNA-specific rqRT-PCR performed on splenocytes co-stimulated ex vivo.

Clonal Tracking of Repopulating Cells in BLT Mice

Tracking of repopulating cells by monitoring vector integration sites (VIS) is a powerful method to monitor the behavior of individual repopulating HSPC clones, for example, to enumerate the number, frequency, longevity, lineage representation of clones, and evidence for aberrant clonal growth. One may use high-throughput methods known in the art. For example, the lineage potential of individual HSPC clones can be determined by fractionation of T-cell (CD3+), B-cell (CD19+), and monocytes (CD14+) from spleen, bone marrow where a sufficient number of cells can be obtained for FACS sorting, followed by a PQCT assay for VIS tracking One may utilize at least 5 animals transplanted for 20-25 weeks following transplant with CAR vector and controls. One may determine the relative number, frequency, and lineage distribution of clones using the PQCT assay. Due to antigen-driven immune cell proliferation, single or pauci-clonal outgrowth of normal transgenic T-cells may occur. This type of expansion can be distinguished from potential malignant transformation by a detailed investigation including blast analysis, karyotype and marker analysis, genomic position of VIS for oncogene activation, and by gene profile analysis. Vector and HIV integration sites can be distinguished by signature mutations within the LTR. Similar analyses can be performed in $T_{SCM}$ transplants to monitor differentiation of $T_{SCM}$ clones to progeny $T_{EM}$ and $T_{CM}$.

Bioinformatics Analysis

Virus integration site (VIS) sequence data can be analyzed by aligning onto the human reference genome (hg19) with Burrows-Wheeler Aligner or BLAT (genome.ucsc.edu) by comparing all sequence reads with Blast software. Homopolymer error correction (454 reads), sequence filtering, sorting, and enumeration may performed by custom-made scripts, e.g., those as described previously (Kim S, et al. Journal of Virology. 2010; 84(22):11771-80). Evidence for insertional mutagenesis through VIS integration sites can be analyzed by applying the method of Bayesian Change-Point model to the z-scores (Presson A, et al. BMC Bioinformatics. 2011; 12(1):367).

In Vivo Activity in the NHP Model

The engraftment of CAR-transduced HSCs can be assayed in a NHP model using methods known in the art.

For example, the ability of autologous, HSCs transduced with a CAR construct according to the present invention to 1) engraft in pigtailed macaques, and 2) produce a measurable decrement in plasma viral load following SHIV challenge may be examined using methods known in the art.

To generate cells expressing the optimized CAR- or control vector in every hematopoietic lineage, one may collect, transduce, and reinfuse autologous HSCs from mobilized bone marrow. Briefly, bone marrow hematopoietic cells may be mobilized by administration of granulocyte colony stimulating factor (GCSF) and stem cell factor (SCF). Bone marrow aspirates will then be collected, enriched for CD34$^+$ HSCs, and transduced with CAR or control lentiviral vectors. During manipulation of HSCs ex vivo, each animal will receive a myeloablative conditioning regimen consisting of 1020 cGy total body irradiation. Following conditioning, transduced HSCs are reinfused into the animal.

Engraftment and animal recovery are monitored after transplant, focusing on an expected reconstitution of neutrophil and platelet counts 20-30 days after transplant, and CD4/CD8 T-cell reconstitution over the first 3 months. Any adverse events will closely be monitored in the animals, including any clinical symptoms indicating any alterations in cytokine levels or clonal cell expansion. These are not anticipated, based on the safety from greater than 500 patient years in the use of the lentiviral vectors in peripheral T cells. Using established markers for each hematopoietic subset, including CD3, CD4, CD8, CD14, CD11c, CD56, and CD19, engraftment of CAR- or vector control-containing cells in each hematopoietic lineage can be demonstrated.

Lymphocyte recovery is expected to be observed approximately 3 months after transplant. Following demonstration of engraftment and CAR marking in hematopoietic subsets, both CAR-expressing animals and vector control animals are challenged with 10,000 TCID50 of SHIV-C. The viral loads in CAR-expressing and control animals are compared and positive selection for gene-marked cells in each condition is monitored.

PBMCs from CAR-containing and control animals are assessed for polyfunctional responses to infected cells as described above. PBMCs are stimulated with irradiated SHIV infected or uninfected cells and assessed for the expression of CD4, CD8 and interferon-gamma (IFN-γ), IL-2, tumor necrosis factor alpha, CD107a, and MIP-1β by flow cytometry.

The dominant viral quasispecies in the peripheral blood for mutations in the CD4 binding domain of the gp120 envelope protein is monitored. The significant development of escape mutations is not expected, since the SHIV requires CD4 binding for cell entry. Viral escape is monitored by direct RT-PCR based sequencing of the dominant quasispecies in the plasma.

Following transduction of enriched HSCs as described above, the efficiency of CAR- or control gene marking in bulk leukocytes and hematopoietic subsets is assayed by flow cytometry and PCR-based methods in the art. A greater than 5% gene marking in bulk leukocytes is expected based on past results with lentiviral transduction of macaque CD34+ HSCs. Between 1 and 3 months post-transplant, a more detailed determination regarding gene marking in reconstituted hematopoietic subsets, including T-cells, B-cells, monocyte/macrophages, granulocytes, and NK cells, may be made. Based on past results, it is expected that CAR expression will be qualitatively comparable in each subset examined.

Approximately 3 months after transplant, animals are challenged with SHIV-C by intravenous injection. Past findings in unprotected animals demonstrate peak viremia of $1\text{-}2 \times 10^7$ viral RNA copies per mL plasma at 2 weeks after challenge; a viral set point of $10^5$ copies/mL is usually reached within 8-10 weeks of challenge. CAR constructs according to the present invention, when expressed successfully, should provide a significant decrease in peak viral load and/or viral set point following SHIV challenge. In addition, enrichment for CAR-protected T-cells after challenge should be observed, since unprotected will be lost to infection.

Therapeutics

One may genetically engineer and enhance the human cellular immune response against HIV using virus-specific CARs according to the present invention. In some embodiments, these CARs are engineered T-cell receptors (TCRs) comprising or consisting of an HIV envelope recognition domain, a transmembrane domain, and an intracellular signaling domain that direct T-cells to kill HIV-infected cells. In some embodiments, the CARs are expressed within a lentiviral vector together with two shRNAs, sh1005 and sh516 and/or other gene reagents, which protect transduced cells from HIV infection.

Desired Dose, Route, and Regimen

In some embodiments, dosing entails a one-time procedure involving stem cell mobilization, purification, culture, lentiviral transduction, and infusion. Transduction would be into either or both HSPC or $T_{SCM}$. This therapy would work well at low-level transduced cell engraftment that limits other stem cell therapeutic approaches due to the fact that CAR-containing T-cells are expected to proliferate in the periphery in response to HIV antigens, like normal T-cells that start at a frequency of 1 per million. This harnesses the natural proliferative capacity of stem cells and mature T-cell progeny to generate key antiviral effector cells. Transplant could be further combined with engineering of HSPC with a lentiviral vector expressing only shRNAs to repopulate with a chimeric hematopoietic system consisting of an HIV-resistant immune system and CAR effector T-cells.

The present invention may be used to design a multi-pronged approach for clinical use of anti-HIV transgenes through combinations of the following therapeutic vectors and cell delivery vehicles in order to optimize anti-HIV efficacy: CAR/shRNAs in HSPC; CAR/shRNAs in $T_{SCM}$; and shRNAs in HSPC. Information regarding each stem cell type is provided below.

Preliminary Preclinical Safety Profile Studies

Stem cell therapy involves the introduction of therapeutic genes potentially over the life of an individual. As such, cytotoxicity or genotoxicity should be evaluated. New signaling activity of CARs or off-target effects of shRNA may skew normal hematopoiesis and/or immune function. The following assays can be used for evaluation of safety/toxicity.

In Vitro Toxicity to Cells and Interferon Responses

Interferon responses can be induced by viruses and double-stranded RNA, and can cause adverse effects due to cell death and inflammation. One may measure evidence of cell death using, e.g., the Promega CytoTox-Glo assay (intracellular protease release) and induction of interferon response gene OAST using, e.g., the SBI Interferon Response Detection Kit (quantitative RT-PCR analysis of IFN-inducible genes).

Genotoxicity—Potential for Insertional Mutagenesis

Lentiviral vectors have demonstrated a strong safety profile in clinical trials with more than 265 patient-years of data with no treatment related serious adverse events reported (virxsys.com/pages/technology-platforms/lentiviral-vector-platform.php). Nevertheless, the impact of vector integration on gene expression and cell functions may be assayed using methods known in the art. Additionally, one may monitor the repopulating clones using methods known in the art, e.g., VIS as described above. Generally, polyclonal, multi-lineage, multi-tissue repopulation without aberrant clonal dominance is desirable.

Adverse Effects on Gene Expression

Off-target effects and signaling defects may result from shRNA and CAR transgene expression. To minimize shRNA off-target effects, one may specifically screen for potent shRNAs using transcriptionally weaker promoters (H1 and 7SK). No adverse effects have been observed of the dual sh1005/sh516 transduced T-cells in vitro or in HSPC during in vivo multi-lineage hematopoietic differentiation in BLT mice.

Gene profile analysis may be conducted if desired, e.g., if aberrant phenotypes are observed in mice. Genes which are over- or under-expressed can be correlated through bioinformatics analysis with the genomic integration sites, cell surface markers assayed by flow cytometry, by canonical pathway analysis (Ingenuity) and homologies between sh1005 and sh516 and sequences within genes that are under-expressed analyzed by the BLAST program (//blast.ncbi.nlm.nih.gov/). One may use a vector without the EGFP reporter gene to utilize a vector suitable for clinical studies. One may follow vector-transduced cells through the identification of the specific CAR by flow cytometry or cellular labeling; for instance, flow cytometry for a specific immunoglobulin extracellular domain if characterizing a CAR that contains this in the HIV recognition domain.

LITERATURE

1. An D, et al. Molecular Therapy. 2006; 14 (4): 494-504.
2. An D, et al. PNAS. 2007; 104 (32): 13110-5.
3. Baroncelli, S., et al. Expert Rev Vaccines. 2008; 7: 1419-1434.
4. Beard, B. C., et al. Journal of Clinical Investigation. 2010; 120: 2345-2354.
5. Berry C, et al. Bioinformatics. 2012; 28 (6): 755-62.
6. Biffi A, et al. Blood. 2011; 117 (20): 5332-9.
7. Brady T, et al. Nucleic Acids Research. 2011; 39 (11): e72.
8. Brainard et al., J. Virol. 2009; 83: 7305-7321.
9. Bushman F, et al. Nature Reviews: Microbiology. 2005; 3 (11): 848-58.
10. Cartier N, et al. Science. 2009; 326 (5954): 818-23.

11. Cavazzana-Calvo M, et al. Nature. 2010; 467 (7313): 318-22.
12. Cieri N, et al. Blood. 2013; 121 (4): 573-84.
13. Deeks S, et al. Molecular Therapy. 2002; 5 (6): 788-97.
14. Deere, J. D., et al. Current opinion in HIV and AIDS. 2011:6; 57-61.
15. DiGiusto D, et al. Science Translational Medicine. 2010; 2 (36): 36ra43.
16. Douek et al., Lancet. 2000; 355: 1875-1881.
17. Egelhofer M, et al. Journal of Virology. 2004; 78 (2): 568-75.
18. Gattinoni L, et al. Nature Medicine. 2009; 15 (7): 808-13.
19. Gattinoni L, et al. Nature Medicine. 2011; 17 (10): 1290-7.
20. Gattinoni L, Restifo N. Blood. 2013; 121 (4): 567-8.
21. Gerrits A, et al. Blood. 2010; 115 (13): 2610-8.
22. Gori, J. L., et al. Blood. 120, e35-44 (2012).
23. Harouse, J. M., et al. Journal of Virology. 2001; 75: 1990-1995.
24. Hildinger, M., et al. Journal of Virology. 2001; 75: 3038-3042.
25. Ho, O., et al. Retrovirology. 2009; 6: 65.
26. Humbert, M., et al. Retrovirology. 2008; 5: 94.
27. Ji H B G A, et al. Journal of Biological Chemistry. 2002; 277 (49): 47898-906.
28. Kalams S, et al. J Virology. 1999; 73 (8): 6715-20.
29. Kiem, K R, et al. Stem Cell. 2012; 10: 137-147.
30. Kilby, J. M., et al. Nature Medicine. 1998; 4: 1302-1307.
31. Kim S, et al. Journal of Virology. 2010; 84 (22): 11771-80.
32. Kimpel, J., et al. PLoS One. 2010; 5: e12357.
33. Kitchen S, et al. PLoS One. 2009; 4 (12): e8208.
34. Kitchen S, et al. PLoS Pathogens. 2012; 8 (4): e1002649.
35. Kitchen S, et al. PNAS USA. 2004; 101 (23): 8727-32.
36. Kitchen, S., et al. J Virol. 1998; 72: 9054-9060.
37. Kong S, et al. Clinical Cancer Research. 2012; 18 (21): 5949-60.
38. Lalezari, J. P., et al. Antiviral Therapy. 2003; 8: 279-287.
39. Lalezari, J. P., et al. New England Journal of Medicine. 2003; 348: 2175-2185.
40. Lazzarin, A., et al. New England Journal of Medicine. 2003; 348: 2186-2195.
41. Li H, Durbin R. Bioinformatics. 2009; 25 (14): 1754-60.
42. Lipowska-Bhalla G, et al. Cancer Immunology and Immunotherapy. 2012; 61 (7): 953-62.
43. Lu R, et al. Nature Biotechnology. 2011; 29 (10): 928-33.
44. Lugli E, et al. Nature Protocol. 2013; 8 (1): 33-42.
45. Marsden M, et al. Journal of Virology. 2012; 86 (1): 339-47.
46. Matsumoto, Y., et al. The Journal of Veterinary Medical Science/Japanese Society of Veterinary Science. 2010; 72: 1057-1061.
47. Mitsuyasu, R. T., et al. Blood. 2000; 96: 785-793.
48. Morrison S. Annual Review in Immunology. 1992; 10: 239-65.
49. Nishimura, Y., et al. Journal of Virology. 2010; 84: 4769-4781.
50. Norris P, et al. Journal of Virology. 2004; 78 (16): 8844-51.
51. Pahar, B., et al. Virology. 2007; 363: 36-47.
52. Pahar, B., European Journal of Immunology. 2006; 36: 583-592.
53. Pal, R., et al. Journal of Acquired Immune Deficiency Syndromes. 2003; 33: 300-307.
54. Polacino, P., et al. Journal of Medical Primatology. 2008; 37 Suppl 2: 13-23.
55. Presson A, et al. BMC Bioinformatics. 2011; 12 (1): 367.
56. Purcell D F, Martin M A. J Virol. 1993; 67 (11): 6365-78.
57. Restifo N, et al. Nature Reviews: Immunology. 2012; 12 (4): 269-81.
58. Ringpis G, et al. PLoS One. 2012; 7 (12): e53492.
59. Roberts, M. R., et al. Blood. 1994; 84: 2878-2889.
60. Rosenberg E, et al. Science. 1997; 278 (5342): 1447-50.
61. Sadelain, R., et al. Cancer Discov. 2013; 3: 388-398.
62. Sakuma, T., et al. Biochemical Journal. 2012; 443: 603-618.
63. Savoldo B, et al. Journal of Clinical Investigation. 2011; 121 (5): 1822-6.
64. Schmidt M, et al. Nature Methods. 2007; 4 (12): 1051-7.
65. Severino, M. E., et al. Virology. 2003; 306: 371-375.
66. Shimizu S, et al. Blood. 2010; 115 (8): 1534-44.
67. Shimizu S, et al. Genetic Vaccines and Therapy. 2009; 7: 8.
68. Shirasu N, Kuroki M. Anticancer Research. 2012; 32 (6): 2377-83.
69. Scholler et al., Science Translational Medicine. 2012; 4: 132ra53-132ra53.
70. Song, R. J., et al. Journal of Virology. 2006; 80: 8729-8738.
71. Stauss H, et al. Molecular Therapy. 2007; 15 (10): 1744-50.
72. Trobridge G, et al. PLoS One. 2009; 4 (11): e7693.
73. Trobridge, G., et al. Blood. 2008; 111: 5537-5543.
74. Trobridge, G. D. & Kiem, H. P. Gene Therapy. 2010; 17: 939-948.
75. Tsai, L., et al. Virology. 2007: 362; 207-216.
76. Van Lunzen J, et al. Molecular Therapy. 2007; 15 (5): 1024-33.
77. Van Rompay, K. K. AIDS Research and Human Retroviruses. 2012: 28; 16-35.
78. Vatakis D, et al. PNAS USA. 2011; 108 (51): e1408-16.
79. Vlasak, J. & Ruprecht, R. M. Aids. 2006; 20: 2135-2140.
80. Walker R, et al. Blood. 2000; 96 (2): 467-74.
81. Wang, X., et al. Blood. 2008; 112: 4981-4990.
82. Watts, K. L., et al. Human Gene Therapy. 2011; 22: 1475-1482.
83. Wild, C. T., et al. PNAS USA. 1994; 91: 9770-9774.
84. Wilkie S, et al. Journal of Clinical Immunology. 2012; 32 (5): 1059-70.
85. Wu C, et al. Human Gene Therapy. 2013; 24 (1): 38-47.
86. Yang O, et al. PNAS USA. 1997; 94 (21): 11478-83.
87. Yang O. Methods in Molecular Biology. 2009; 485: 407-15.
88. Zhang Y, et al. Nature Medicine. 2005; 11 (12): 1299-305.

To the extent necessary to understand or complete the disclosure of the present invention, all publications, patents, and patent applications mentioned herein are expressly incorporated by reference therein to the same extent as though each were individually so incorporated. It should be noted that the inclusion of references to journal articles throughout the specification shall not be construed as any admission that the methods and compositions of the present invention are anticipated and/or obvious.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A recombinant progenitor cell which comprises a stem cell transduced with a vector containing a nucleic acid molecule that encodes a truncated chimeric antigen receptor (CAR), which comprises a truncated CD4, which has a D1 extracellular domain and lacks at least one extracellular domain selected from D2, D3, and D4, fused to a signaling domain of a CD3 complex ζ-chain and said CAR is specific for a virus or an epitope thereof, wherein the recombinant progenitor cell is capable of differentiating into a functional effector cell.

2. The recombinant progenitor cell of claim 1, wherein the nucleic acid molecule is contained within a CAR construct.

3. The recombinant progenitor cell of claim 1, wherein the stem cell is a hematopoietic stem cell or a hematopoietic progenitor cell.

4. The recombinant progenitor cell of claim 3, wherein the stem cell is a memory T stem cell.

5. The recombinant progenitor cell according to claim 1, wherein the vector is a lentiviral vector.

6. The recombinant progenitor cell of claim 1, wherein the truncated CD4 CAR has an extracellular domain that binds gp120 expressed on the surface of cells infected with HIV.

7. The recombinant progenitor cell according to claim 1, wherein the virus is a lentivirus.

8. The recombinant progenitor cell of claim 7, wherein the lentivirus is a human immunodeficiency virus.

9. The recombinant progenitor cell according to claim 1, wherein the functional effector cell is a T-cell.

10. The recombinant progenitor cell of claim 9, wherein the T-cell expresses the truncated CAR on its cell surface.

11. The recombinant progenitor cell according to claim 1, wherein the vector further comprises one or more genetic sequences which protect the recombinant progenitor cell from infection by the virus.

12. The recombinant progenitor cell of claim 11, wherein the genetic sequences are selected from the group consisting of: sh1005, sh516, and a nucleic acid molecule encoding C46, and the virus is a human immunodeficiency virus.

13. A method of producing a functional effector cell which comprises differentiating or developing the recombinant progenitor cell of claim 1 and then maturing it into the functional effector cell.

14. The method of claim 13, wherein the recombinant progenitor cell is administered to or engrafted in a subject.

15. An engineered functional effector cell made by the method according to claim 13.

16. The engineered functional effector cell of claim 15, which expresses a truncated CAR on its cell surface.

17. A method of inhibiting, reducing or treating a viral infection in a subject which comprises administering the recombinant progenitor cell according to claim 1 or a functional effector cell matured therefrom to the subject.

18. The recombinant progenitor cell according to claim 1, wherein the recombinant progenitor cell lacks HLA-restricted T cell receptors.

19. A nucleic acid molecule comprising a sequence encoding a truncated chimeric antigen receptor (CAR), which comprises a truncated CD4 which has a D1 extracellular domain and lacks at least one extracellular domain selected from D2, D3, and D4, fused to the signaling domain of the CD3 complex ζ-chain.

20. The nucleic acid molecule of claim 19, wherein the nucleic acid molecule encodes a truncated Double CAR, a truncated Triple CD4ζ CAR, CD4D1D2D3CAR, CD4D1D2CAR, or CD4D1CAR.

21. The nucleic acid molecule of claim 19, wherein the nucleic acid molecule contains a nucleotide sequence encoding a single chain antibody having an amino acid sequence selected from the group consisting of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; and SEQ ID NO:15.

22. The recombinant progenitor cell of claim 1, wherein the stem cell is a human stem cell.

23. The nucleic acid molecule of claim 19, wherein the nucleic acid molecule further comprises a nucleotide sequence encoding C46 fusion inhibitory antiviral peptide.

24. The nucleic acid molecule of claim 19, wherein the nucleic acid molecule further comprises an antiviral shRNA.

25. An engineered functional effector cell that expresses on its cell surface a truncated chimeric antigen receptor (CAR), which comprises a truncated CD4, which has a D1 extracellular domain and lacks at least one extracellular domain selected from D2, D3, and D4, fused to the signaling domain of the CD3 complex ζ-chain.

26. An engineered functional effector cell that expresses on its cell surface a chimeric antigen receptor (CAR) comprising a single chain antibody having an amino acid sequence selected from the group consisting of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; and SEQ ID NO:15.

\* \* \* \* \*